(12) United States Patent
Colletti et al.

(10) Patent No.: US 6,399,786 B1
(45) Date of Patent: Jun. 4, 2002

(54) NONACYCLIC NODULISPORIC ACID DERIVATIVES

(75) Inventors: Steven L. Colletti, Princeton Junction; Michael H. Fisher, Ringoes; Peter T. Meinke, Plainfield; Matthew J. Wyvratt, Mountainside, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/901,264

(22) Filed: Jul. 9, 2001

Related U.S. Application Data

(60) Provisional application No. 60/218,183, filed on Jul. 14, 2000.

(51) Int. Cl.[7] ...................... A61K 31/407; A61P 33/10; C07D 491/052
(52) U.S. Cl. ...................... 548/417; 549/381; 549/414; 549/472; 549/473; 549/59; 549/60; 548/417; 514/410; 514/422; 514/423; 514/444; 514/453; 514/461

(58) Field of Search .................. 549/356, 381, 549/414, 472, 473, 59, 60; 548/417; 514/410, 422, 423, 444, 453, 461

(56) References Cited

U.S. PATENT DOCUMENTS

| | | | | |
|---|---|---|---|---|
| 5,399,582 A | * | 3/1995 | Dombrowski et al. | 514/410 |
| 5,595,991 A | * | 1/1997 | Shoop et al. | 514/233.2 |
| 5,962,499 A | * | 10/1999 | Meinke et al. | 514/410 |
| 6,221,894 B1 | | 4/2001 | Meinke et al. | |

* cited by examiner

*Primary Examiner*—Floyd D. Higel
*Assistant Examiner*—Golam M. M. Shameem
(74) *Attorney, Agent, or Firm*—David L. Rose; Mollie M. Yang

(57) ABSTRACT

The present invention relates to novel nodulosporic acid derivatives, which are acaricidal, antiparasitic, insecticidal and anthelmintic agents.

17 Claims, No Drawings

NONACYCLIC NODULISPORIC ACID DERIVATIVES

This application claims priority under U.S. provisional application 60/218,183 filed on Jul. 14, 2000, which is hereby incorporated by reference in its entirety.

BACKGROUND OF THE INVENTION

Nodulisporic acid is an antiparasitic agent and ectoparasiticidal agent isolated from the fermentation culture of Nodulisporium sp. MF-5954 (ATCC 74245), and having the following structure:

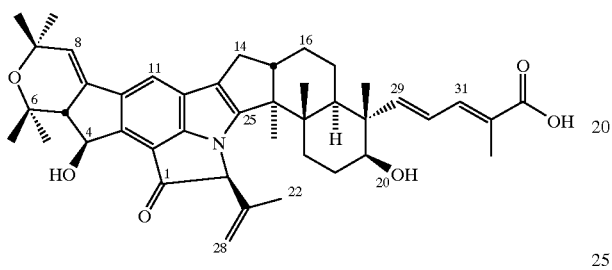

Nodulisporic acid is disclosed as "Compound 1" in U.S. Pat. No. 5,399,582. Also disclosed therein are "Compound 2" and "Compound 3":

"Compound 2"

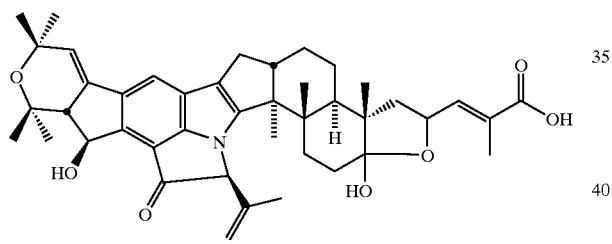

"Compound 3"

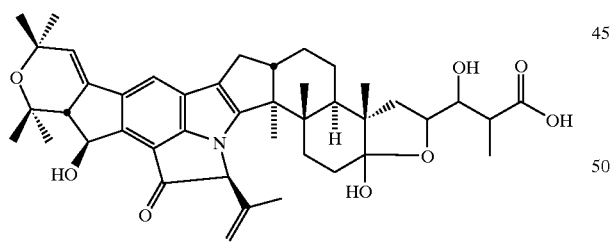

Derivatives of nodulisporic acid are disclosed in U.S. Pat. No. 5,962,499.

SUMMARY OF THE INVENTION

This invention relates to new acaricidal, antiparasitic, insecticidal and anthelmintic agents related to the nodulisporic acids, to processes for their preparation, compositions thereof, their use in the treatment of parasitic infections, including helminthiasis, in human and animals, and their use in the treatment of parasitic infections in plants or plant products.

DETAILED DESCRIPTION OF THE INVENTION

The present invention provides compounds having the formula I:

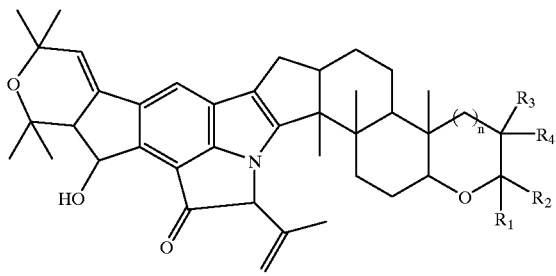

wherein
$R_1$ is
(1) hydrogen,
(2) C(O)H,
(3) optionally substituted $(C=O)_p$—$R^x$, wherein the substituent is one to ten groups independently selected from $R^z$, $OR^a$, $OC(O)R^b$, $CO_2R^b$, $NR^cCOR^d$, $CONR^cR^d$, and $NR^cR^d$,
(4) $C_1$–$C_{10}$alkoxy,
(5) $C_1$–$C_{10}$alkylthio,
(6) $CO_2R^b$,
(7) $CONR^cR^d$,
(8) $CONR^cSO_2R^d$,
(9) CN,
$R_2$ is
(1) hydrogen,
(2) $OR^a$,
(3) $SR^a$; or
$R_1+R_2$ represent =O; or
$R_1$ and $R_2$ together with the carbon atom to which they are attached form a 5- to 7-membered ring containing 0 to 2 heteroatoms selected from O, $S(O)_m$ and N, optionally substituted with 1 to 4 groups independently selected from $R^a$;
$R_3$ is
(1) hydrogen,
(2) $OR^a$,
(3) $NR^cR^d$,
(4) $NR^cOR^d$,
(5) $NR^cSO_2R^d$,
(6) $NR^eCONR^cR^d$,
(7) $NR^cCO_2R^d$; or
$R_2+R_3$ represent a bridging oxygen atom;
$R_4$ is hydrogen, or
$R_2$ and $R_4$ together represents a bond between the carbon atoms to which they are attached;
$R^a$ is
(1) H,
(2) optionally substituted $R^y$,
(3) optionally substituted $C(O)R^x$,
(4) $PO(OR^b)_2$,
(5) $SO_2R^b$,
(6) a natural or unnatural mono-, di- or tri-saccharide composed of any furanose or pyranose, or combination thereof; wherein said substituent for $R^x$ and $R^y$ are 1 to 10 groups independently selected from $R^z$, hydroxy, $C_1$–$C_6$alkoxy, $OC(O)R^b$, $CO_2R^b$, $NR^cCOR^d$, $CONR^cR^d$, and $NR^cR^d$,
$R^b$ is
(1) hydrogen
(2) optionally substituted $R^y$, wherein said substituents are 1 to 10 groups independently selected from $R^z$, hydroxy, $C_1$–$C_6$ alkoxy, OC(O)$C_1$–$C_6$alkyl, carboxy, $CO_2C_1$–$C_6$alkyl, NR$^c$COR$^d$, CONR$^c$R$^d$, and NR$^c$R$^d$, (3) a natural or unnatural mono-, di- or tri-saccharide composed of any furanose or pyranose, or combination thereof;

R$^c$ is
(1) hydrogen,
(2) optionally substituted R$^y$, wherein said substituents are 1 to 10 groups independently selected from R$^z$, hydroxy, $C_1$–$C_6$alkoxy, OC(O)$C_1$–$C_6$alkyl, carboxy, $CO_2C_1$–$C_6$alkyl, NHCO$C_1$–$C_6$alkyl, CONH($C_1$–$C_6$alkyl), NH$_2$, NH($C_1$–$C_6$alkyl), N($C_1$–$C_6$alkyl)$_2$, R$^d$ is independently selected from R$^c$; or R$^c$ and R$^d$ together with the N to which they are attached form a 3- to 10-membered ring containing 0 to 2 additional heteroatoms selected from O, S(O)$_m$ and N, optionally substituted with 1 to 4 groups independently selected from R$^e$;

R$^e$ is halogen, cyano, oxo or optionally substituted R$^x$ wherein said substituents are 1 to 10 groups independently selected from R$^z$, hydroxy, $C_1$–$C_6$alkoxy, OC(O)$C_1$–$C_6$alkyl, carboxy, $CO_2C_1$–$C_6$alkyl, NHCO$C_1$–$C_6$alkyl, CONH($C_1$–$C_6$alkyl), NH$_2$, NH($C_1$–$C_6$alkyl), N($C_1$–$C_6$alkyl)$_2$, R$^x$ is
(1) $C_1$–$C_{10}$ alkyl,
(2) $C_2$–$C_{10}$ alkenyl,
(3) $C_2$–$C_{10}$ alkynyl,
(4) $C_3$–$C_8$ cycloalkyl,
(5) $C_5$–$C_8$ cycloalkenyl,
(6) aryl,
(7) a 5- or 6-membered heterocycle containing from 1 to 4 heteroatoms selected from oxygen, sulfur and nitrogen;

R$^y$ is
(1) $C_1$–$C_{10}$ alkyl,
(2) $C_3$–$C_{10}$ alkenyl,
(3) $C_3$–$C_{10}$ alkynyl,
(4) $C_3$–$C_8$ cycloalkyl,
(5) $C_5$–$C_8$ cycloalkenyl,
(6) aryl,
(7) a 5- or 6-membered heterocycle containing from 1 to 4 heteroatoms selected from oxygen, sulfur and nitrogen;

R$^z$ is
(1) $C_1$–$C_5$ alkyl,
(2) $C_2$–$C_5$ alkenyl,
(3) $C_3$–$C_8$ cycloalkyl,
(4) aryl, optionally substituted by 1 to 4 groups selected from $C_1$–$C_5$ alkyl, $C_2$–$C_5$ alkenyl, $C_1$–$C_5$ alkoxy, hydroxy, amino, cyano, halogen, OC(O)$C_1$–$C_6$alkyl, carboxy, Co$_2C_1$–$C_6$alkyl, NHCO$C_1$–$C_6$alkyl, CONH($C_1$–$C_6$alkyl), NH($C_1$–$C_6$alkyl), N($C_1$–$C_6$alkyl)$_2$,
(5) halogen,
(6) cyano,
(7) oxo,
(8) a 5- or 6-membered heterocycle containing from 1 to 4 heteroatoms selected from oxygen, sulfur and nitrogen optionally substituted by 1 to 4 groups selected from $C_1$–$C_5$ alkyl, $C_2$–$C_5$ alkienyl, $C_1$–$C_5$ alkoxy, hydroxy, oxo, amino, cyano, halogen, OC(O)$C_1$–$C_6$alkyl, carboxy, $CO_2C_1$–$C_6$alkyl, NHCO$C_1$–$C_6$alkyl, CONH($C_1$–$C_6$alkyl), NH($C_1$–$C_6$alkyl), N($C_1$–$C_6$alkyl)$_2$, m is 0 to 2;
n is 0 or 1;
p is 0 or 1; or
a pharmaceutically acceptable salt thereof.

The present invention provides in another aspect pharmaceutical compositions comprising a compound of Formula I and a pharmaceutically acceptable carrier. Such compositions may further comprise one or more other active ingredients such as anthelmintic agents, insect regulators, ecdosyne agonists and fipronil.

The present invention provides in another aspect a method for treating parasitic diseases in a mammal which comprises administering an antiparasitic amount of a compound of Formula I. The treatment may further comprise co-administering one or more other active ingredients such as anthelmintic agents, insect regulators, ecdosyne agonists and fipronil.

In one subset of compounds of formula I, n is 0.

In another subset of compounds of formula I, n is 1.

In another subset of compounds of formula I, $R_1$ is H, and $R_2$ is H, OR$^a$ or SR$^a$. Preferably, $R_2$ is OR$^a$ or SR$^a$ wherein R$^a$ is H, optionally substituted $C_1$–$C_6$alkyl, optionally substituted $C_3$–$C_6$alkenyl, or optionally substituted aryl, wherein the substituent is 1 to 4 groups independently selected from R$^z$, hydroxy, $C_1$–$C_6$alkoxy, OC(O)R$^b$, CO$_2$R$^b$, NR$^c$COR$^d$, CONR$^c$R$^d$, and NR$^c$R$^d$. Examples of $R_2$ include, but are not limited to, hydrogen, hydroxy, methoxy, ethoxy, n-propoxy, isopropoxy, t-butoxy, allyloxy, 6-methoxycarbonyl-n-hexyloxy, benzyloxy, 2-oxo-5-pyrrolidinylmethoxy, 2-acetamidoethoxy, 2-methyl-2-acetylethoxy, 2-(2-oxo-1-pyrrolidinyl)ethoxy, 2-(2,5-dioxo-1-pyrrolidinyl)ethoxy, 2-cyanoethoxy, 3-furanyl-methoxy, 4-imidazolylmethoxy, 2-(4-methyl-5-thiazolyl)ethoxy, methylthio, ethylthio, phenylthio, 2-methoxyphenylthio.

In another subset of compounds of formula I, $R_2$ is H, and $R_1$ is R$^x$, optionally substituted with one to ten groups independently selected from R$^z$, OR$^a$, OC(O)R$^b$, CO$_2$R$^b$, NR$^c$COR$^d$, CONR$^c$R$^d$, and NR$^c$R$^d$. In one embodiment $R_1$ is selected from $C_{1-6}$alkyl, $C_{3-6}$alkenyl and aryl. Examples of $R_1$ include, but are not limited to, methyl, allyl, 2-thienyl, 2-furanyl.

In another subset of compounds of formula I, $R_1$ and $R_2$ together is an oxo group.

In another subset of compounds of formula I, $R_2$ and $R_4$ together form a bond across the carbon atoms to which they are attached.

In a preferred embodiment, compounds of formula I have the stereoconfiguratioin is shown:

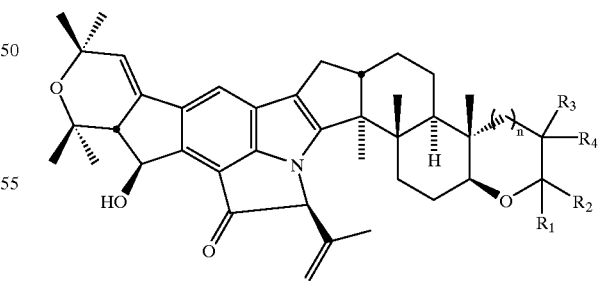

"Alkyl" as well as other groups having the prefix "alk", such as alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond. Examples of alkenyl groups include allyl, homoallyl and the like. Examples of alkynyl groups include propargyl, homopropargyl and the like.

Alkanoyl means alkylcarbonyl in which alkyl is as defined above.

Alkenoyl means alkenylcarbonyl in which alkenyl is as defined above.

The term "cycloalkyl" means carbocycles containing no heteroatoms, and includes mono-, bi- and tricyclic saturated carbocycles, as well as benzofused carbocycles. Examples of cycloalkyl include cyclopropyl, cyclobutyl, cyclopentyl, cyclohexyl, decahydronaphthalene, adamantane, indanyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "halogen" is intended to include the halogen atoms fluorine, chlorine, bromine and iodine.

The term "heterocycle", unless otherwise specified, means mono- or bicyclic compounds that are saturated or partly unsaturated, as well as benzo- or heteroaromatic ring fused saturated heterocycles or partly unsaturated heterocycles, and containing from 1 to 4 heteroatoms independently selected from oxygen, sulfur and nitrogen. Examples of saturated heterocycles include lactams, cyclic imides, morpholine, thiomorpholine, piperidine, piperazine, tetrahydropyran, tetrahydrofuran, dioxane, tetrahydrothiophene, oxazolidine, pyrrolidine; examples of partly unsaturated heterocycles include dihydropyran, dihydropyridazine, dihydrofuran, dihydrooxazole, dihydropyrazole, dihydropyridine, dihydropyridazine and the like. Examples of benzo- or heteroaromatic ring fused heterocycles include 2,3-dihydrobenzofuranyl, benzopyranyl, tetrahydroquinoline, tetrahydroisoquinoline, benzomorpholinyl, 1,4-benzodioxanyl, 2,3-dihydrofuro(2,3-b)pyridyl and the like.

The term "aryl" is intended to include mono- and bicyclic aromatic and heteroaromatic rings containing from 0 to 5 heteroatoms independently selected from nitrogen, oxygen and sulfur. The term "aryl" is also meant to include benzofused ∥cloalkyl, benzofused cycloalkenyl, and benzofused heterocyclic groups. Examples of "aryl" groups include phenyl, pyrrolyl, isoxazolyl, pyrazinyl, pyridinyl, oxazolyl, thiazolyl, imidazolyl, triazolyl, tetrazolyl, furanyl, triazinyl, thienyl, pyrimidinyl, pyridazinyl, pyrazinyl, naphthyl, benzoxazolyl, benzothiazolyl, benzimidazolyl, benzofuranyl, furo(2,3-b)pyridyl, 2,3-dihydrofuro(2,3-b)pyridyl, benzoxazinyl, benzothiophenyl, quinolinyl, indolyl, 2,3-dihydrobenzofuranyl, benzopyranyl, 1,4-benzodioxanyl, indanyl, indenyl, fluorenyl, 1,2,3,4-tetrahydronaphthalene and the like.

Aroyl means arylcarbonyl in which aryl is as defined above.

Examples of $NR^cR^d$ forming a 3- to 10-membered ring containing 0 to 2 additional heteroatoms selected from O, $S(O)m$ and N are aziridine, azetidine, pyrrolidine, piperidine, thiomorpholine, morpholine, piperazine, octahydroindole, tetrahydroisoquinoline and the like.

The term "optionally substituted" is intended to include both substituted and unsubstituted; thus, for example, optionally substituted aryl could represent a pentafluorophenyl or a phenyl ring.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Certain of the above defined terms may occur more than once in the above formula and upon such occurrence each term shall be defined independently of the other; thus, for example, $OR^a$ at $R_2$ may represent $OCH_3$ and at $R_3$ represent OH.

Compounds described herein contain one or more asymmetric centers and may thus give rise to diastereomers and optical isomers. The present invention is intended to include all possible diastereomers as well as their racemic and resolved, enantiomerically pure forms and all possible geometric isomers. In addition, the present invention includes all pharmaceutically acceptable salts thereof. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, thium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumatic, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Compounds of the present invention are prepared from nodulisporic acid, which in turn is obtained from the fermentation culture of Nodulisporium sp. MF-5954 (ATCC 74245). The descriptions of the producing microorganism, the fermentation process, and the isolation and purification of nodulisporic acid are disclosed in U.S. Pat. No. 5,399,582, issued Mar. 21, 1995, which is hereby incorporated by reference in its entirety.

The above structural formula I is shown without a definitive stereochemistry at certain positions. However, during the course of the synthetic procedures used to prepare such compounds, or using racemization or epimerization procedures known to those skilled in the art, the products of such procedures can be a mixture of stereoisomers. In particular, the stereoisomers at C4, C20, C26, C29, C30 and C31 may be oriented in either the alpha- or beta-position, representing such groups oriented below or above the plane of the molecule, respectively. In each such case, and at other positions in the molecule, both the alpha- and beta-configurations are intended to be included within the ambit of this invention.

The carbon atoms within the compounds of the present invention are numbered as indicated in Formulas IIa and IIb, and are directly related to the numbering system of the parent compound, nodulisporic acid.

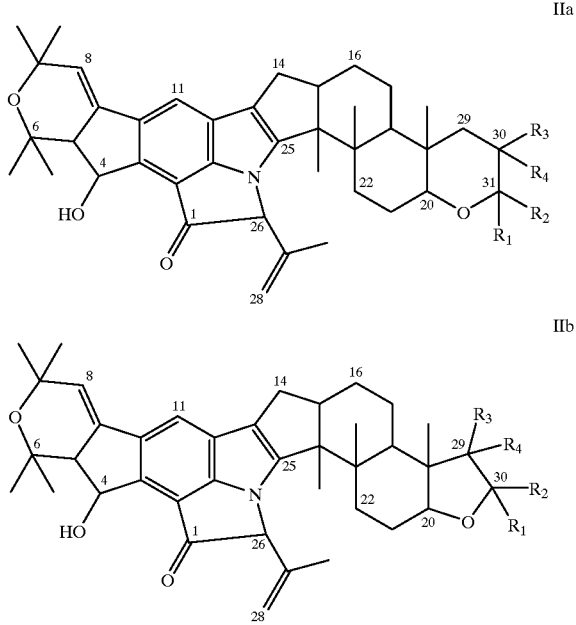

Abbreviation:
DAST: (diethylamino)sulfur trifluoride
DBU: 1,8-diazabicyclo[5.4.0]undec-7-ene
DMF: dimethylformamide
DMSO: dimethylsulfoxide
DPPA: diphenyl phosphoryl azide
Et: ethyl
EtOAc: ethyl acetate
EtOH: ethanol
HMDS: hexamethyldisilazane
iPr: isopropyl
MCPBA: meta-chloroperbenzoic acid
Me: methyl
MeOH: methanol
NBS: N-bromosuccinimide
NMO: N-methylmorpholine-N-oxide
PCC: pyridinium chlorochromate
PPTS: pyridinium para-toluenesulfonic acid
TBHP t-butyl hydroperoxide
TEMPO: 2,2,6,6-tetramethyl-1-piperidinyloxy, free radical
TES: triethylsilyl
Tf: trifluoromethanesulfonyl
THF: tetrahydrofuran
TMS: trimethylsilyl
TPAP: tetrapropylammonium perruthenate
TsOH: para-toluenesulfonic acid Compounds of formula I wherein the propenyl group at position C26 is in the epi configuration, relative to the nodulisporic acid starting material, may be obtained by treatment of the appropriate precursor with a base such as hydroxide, methoxide, imidazole, triethylamine, potassium hydride, lithium diisopropylamide and the like in protic or aprotic solvents (as appropriate) such as water, methanol, ethanol, methylene chloride, chloroform, tetrahydrofuran, dimethylformamide and the like. The reaction is complete at temperatures from −78° C. to the reflux temperature of the solution in from 15 minutes to 12 hours.

The stereoconfiguration at C4 of compounds of formula I may be inverted from that of the nodulisporic acid starting material using protocols known to those skilled in the art. For example, the hydroxy group at C4 may be reacted under Mitsunobu conditions with a carboxylic acid (formic acid, propionic acid, 2-chloroacetic acid, benzoic acid, para-nitrobenzoic acid and the like), a tri-substituted phosphine (triphenylphosphine, tri-n-butylphoshine, tripropylphosphine and the like) and a dialkyl diazodicarboxylate (diethyl diazodicarboxylate, dimethyl diazodicarboxylate, diisopropyl diazodicarboxylate and the like) in an aprotic solvent such as methylene chloride, tetrahydrofuran, chloroform, benzene and the like. The Mitsunobu reactions are complete in from 1 to 24 hours at temperatures from 0° C. to the reflux temperature of the solution. The resultant esters may be hydrolyzed by treatment with hydroxide or ammonium hydroxide in a protic solvent such as methanol, ethanol, water, tetrahydrofuran/water or dimethylformamide/water and the like at from 0° C. to the reflux temperature of the solution. Alternatively, the resultant esters may be hydrolyzed by treatment with a Lewis acid, such as magnesium chloride, aluminum chloride, titanium tetra-isopropoxide and the like in a protic solvent such as methanol, ethanol, isopropanol and the like and the reactions are complete in from 1 to 24 hours at 0° C. to the reflux temperature of the solution.

During certain reactions described below, it may be necessary to protect the hydroxyl groups at C4 and C20 of nodulisporic acid-derived synthetic intermediates, and the hydroxyl group at C4 of formula I. With these positions protected, the reactions may be carried out at other positions without affecting the remainder of the molecule. Subsequent to any of the described reactions (vida infra), the protecting group(s) may be removed and the unprotected product isolated. The protecting groups employed at C4 and C20 are those which may be readily synthesized, not significantly affected by the reactions at the other positions, and may be removed without significantly affecting any other functionality of the molecule. One preferred type of protecting group is the tri-substituted silyl group, preferably the tri-loweralkyl silyl group or di-loweralkyl-aryl silyl group. Especially preferred examples are the trimethylsilyl (TMS), triethylsilyl (TES), triisopropylsilyl, tert-butyldimethylsilyl and dimethylphenylsilyl groups.

The protected compound may be prepared with hexamethyldisilazane (HMDS) or the appropriately substituted silyl trifluoromethanesulfonate or silyl chloride. The reaction is carried out in an aprotic solvent such as methylene chloride, benzene, toluene, ethyl acetate, isopropyl acetate, tetrahydrofuran, acetonitrile, dimethylformamide and the like. In order to minimize side reactions, there can be included in the reaction mixture a base to react with the acid released during the course of the reaction. Preferred bases are amines such as imidazole, pyridine, triethylamine or diisopropylethylamine and the like. The base is required in amounts equimolar to the amount of hydrogen halide liberated, however, generally several equivalents of the amine are employed. The reaction is stirred at from 0° C. to the reflux temperature of the reaction mixture and is complete from 1 to 24 hours.

The silyl group is removed by treatment of the silyl compound with anhydrous pyridine-hydrogen fluoride in tetrahydrofuran or dimethylsulfoxide or with tetraalkylammonium fluoride in tetrahydrofuran. The reaction is complete in from 1 to 24 hours at from 0° C. to 50° C. Alternatively, the silyl group may be removed by stirring the silylated compound in an aprotic solvent such as tetrahydrofuran (TIM), or lower protic solvents such as methanol, ethanol, isopropanol and the like catalyzed by an acid, preferably a sulfonic acid monohydrate such as pyridinium para-toluenesulfonic acid (PPTS), para-toluenesulfonic acid (TsOH), benzenesulfonic acid or carboxylic acids such as acetic acid, propionic acid, monochloroacetic acid, dichloroacetic acid, trichloroacetic acid and the like. The reaction is complete in 1 to 24 hours at from 0° C. to 50° C.

Protecting groups that may also be suitably used in the preparation of compounds of the present invention may be found in standard textbooks such as Greene and Wutz, *Protective Groups in Organic Synthesis,* 1991, John Wiley & Sons, Inc.

Compounds of formula I wherein n is 1, $R_2$ is a hydroxyl, $R_1$, $R_3$ and $R_4$ are hydrogen, may be prepared according to the procedure shown in Scheme 1a. Thus, Compound III, prepared by oxidative cleavage of nodulisporic acid using potassium permanganate or a nodulisporamide using osmium tetroxide, is hydrogenated using conventional procedures known to those skilled in the art to provide hemiacetal VI. The enal double bond may be reduced with any of a variety of standard precious metal hydrogenation catalysts such as Wilkinson's catalyst, Pearlman's catalyst, 1–25% palladium on carbon (Pd—C), 1–25% platinum on carbon and the like. The reaction is generally carried out in non-reducible solvents (either protic or aprotic) such as methanol, ethanol, isopropanol, tetrahydrofuran, isopropyl acetate, benzene, toluene, dimethylformamide and the like. The hydrogen source may be hydrogen gas from 1 to 50 atmospheres of pressure or other hydrogen sources such as ammonium formate, cyclohexene, cyclohexadiene and the like. The reduction also may be carried out using sodium dithionite and sodium bicarbonate in the presence of a phase transfer catalyst, in particular a tetraalkylammonium phase transfer catalyst, and the like. The reactions may be run from 0° C. to 100° C. and are complete in from 5 min to 24 hours. Alternatively, Compound IV, from compound III using HMDS, is hydrogenated under similar conditions described above to provide V. Preferred hydrogenation conditions of HI and IV are 1 atmosphere of hydrogen with catalytic 10% palladium on carbon in ethyl acetate solvent. Compound V is treated with PPTS in TBF to also afford hemiacetal VI.

Scheme 1a

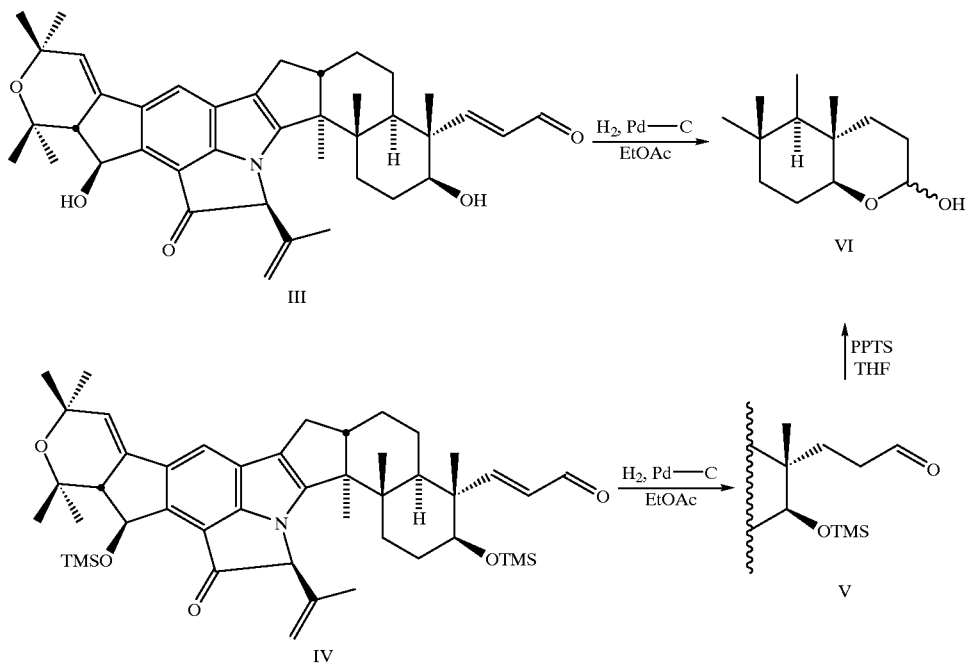

Compounds of formula I wherein n is 0, $R_2$ is a hydroxyl, $R_1$, $R_3$ and $R_4$ are hydrogen, may be prepared according to the procedure shown in Scheme 1b. Thus, Compound XVII is treated with diphenylphosphoryl azide and heated in an aprotic solvent such as, but not restricted to, toluene, resulting in a rearrangement yielding vinyl isocyanate XVIII. Compound XVIII is then converted to hemiacetal XX via treatment with an acid or acid mixture in an aqueous or partially aqueous solvent system. Typical acids used independently or in mixtures with each other for this transformation are sulfonic acid monohydrates such as benzenesulfonic acid, camphor sulfonic acid or carboxylic acids such as acetic acid, propionic acid, monochloroacetic acid, dichloroacetic acid, trichloroacetic acid, trifluoroacetic acid or inorganic acids such as hydrochloric acid, sulfuric acid, polyphosphoric acid and the like. The preferred acid mixture is a combination of pyridinium para-toluenesulfonic acid (PPTS) with a lesser amount of para-toluenesulfonic acid (TsOH). The solvent system used is either water or a mixture of water with organic solvents such as, but not restricted to, tetrahydrofuran, dimethoxyethane, diethyl ether, benzene, toluene, acetonitrile, nitromethane, methylene chloride, chloroform, dimethylformamide, dimethylacetamide, N-methylpyrrolidinone and the like. The preferred solvent system is a mixture of dioxane and water. These hemiacetal-forming reactions may be performed from −20° C. to 100° C. and are complete in 5 minutes to 48 hours.

Scheme 1b

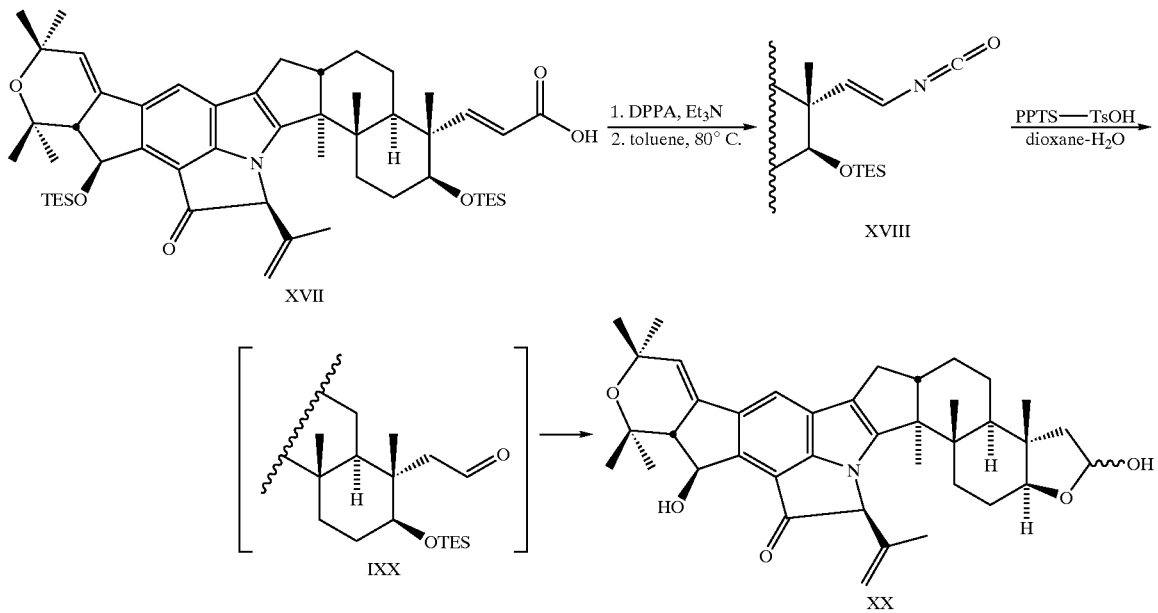

As shown in Scheme 2, the hemiacetal VIa is treated with an organic acid in an alcohol solvent under conditions known to those skilled in the art to yield the acetal VII. Typical organic acids used for this transformation are sulfonic acid monohydrates such as para-toluenesulfonic acid (TsOH), benzenesulfonic acid, camphorsulfonic acid or carboxylic acids such as acetic acid, propionic acid, monochloroacetic acid, dichloroacetic acid, trichloroacetic acid and the like. The preferred organic acid is pyridinium para-toluenesulfonic acid (PPTS). The reaction is complete in 1 to 24 hours at from 0° C. to 50° C.

Similarly, thioacetal Vfi are prepared from thiol under conditions analogous to those described for the preparation of acetal VII. Additionally, an aprotic solvent is used such as dimethylformamide, dimethylacetamide, N-methylpyrrolidinone, tetrahydrofuran, dioxane, benzene, toluene, chloroform, 1,2-dichloroethane and the like. The preferred solvent is methylene chloride.

Scheme 2

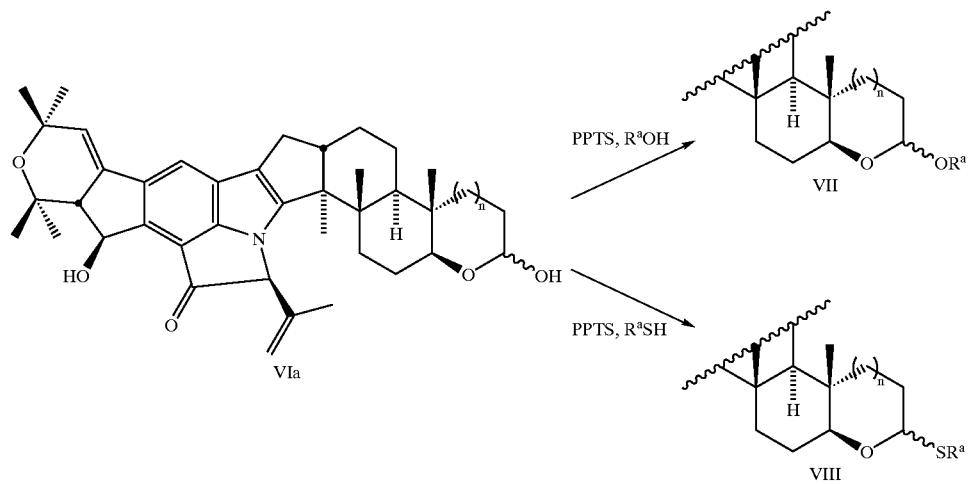

Compounds of formula I wherein $R_1$ and $R_2$ together represent a oxo, (=O), and $R_3$ and $R_4$ are each hydrogen may be prepared by treating the appropriate hemiacetal with an oxidant under conditions known to those skilled in the art to produce the corresponding lactone. For example, hemiacetal VI is oxidized to IX as shown in Scheme 3. Lactone formation may be accomplished by using reagents including, but not restricted to, Dess-Martin periodinane, $SO_3$-pyridine/DMSO, 4-acetamido-TENMPO/para-toluenesulfonic acid, PCC and the like. Unreactive solvents that may be used in the oxidation are chloroform, 1,2-dichloroethane, benzene and the like. The preferred reaction conditions are catalytic tetrapropylammonium perruthenate (TPAP) with the addition of excess co-oxidant, N-methylmorpholine N-oxide, in methylene chloride solvent. The reaction is complete in 1 to 24 hours at from −20° C. to 50° C.

Compounds of formula I wherein $R_1$ is a methyl, $R_3$ is hydrogen, and $R_2$ and $R_4$ together form a bond across the carbon atoms to which they are attached, may be prepared according to the procedure shown in Scheme 4 using conditions known to those skilled in the art. For example, the lactone XII is treated with olefination reagents including, but not restricted to, Tebbe, Wittig, Peterson and the like to yield the methyl glycal XIII. Typical media used for this transformation are aprotic organic solvents such as benzene, mesitylene, diethyl ether, dioxane and the like. The preferred conditions utilize dimethyl titanocene in a solvent mixture of THF and toluene. The reactions are complete in from 1 to 48 hours at −78° C. to the reflux temperature of the solution.

Scheme 3

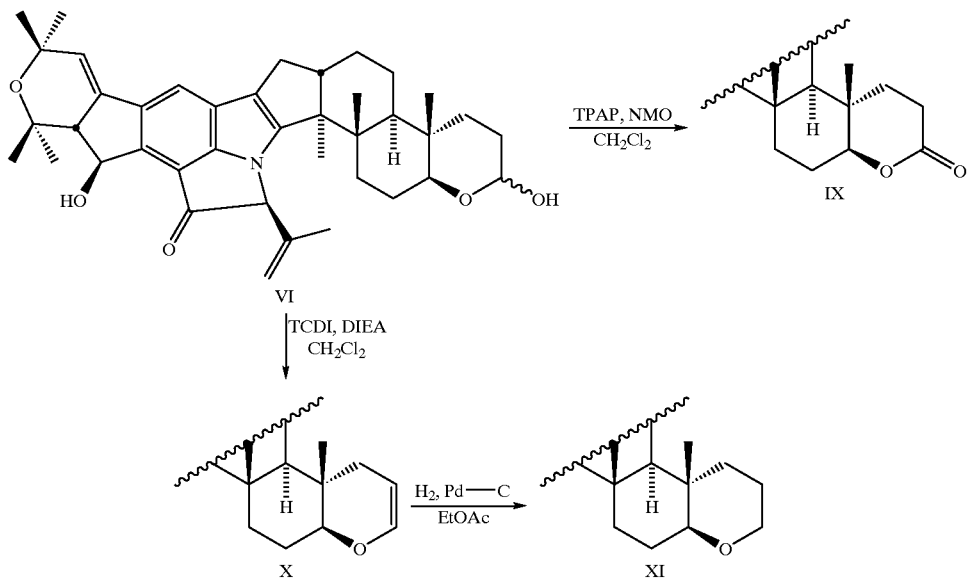

Compounds of formula I wherein $R_1$ and $R_3$ are hydrogen, and $R_2$ and $R_4$ together form a bond across the carbon atoms to which they are attached, may be prepared by treatment of the appropriate hemiacetal with dehydrating reagents known to those skilled in the art such as para-toluenesulfonyl chloride, methanesulfonyl chloride, dinitrobenzenesulfonyl chloride, acetyl chloride, thionyl chloride, Burgess reagent, Martin sulfurane, $Ph_3P$—$CBr_4$-DBU, 4-hydroxymethyleneimidazole-PPTS and the like. The reaction is conducted in a solvent such as chloroform, tetrahydrofuran, dioxane, benzene, toluene and the like, and the reactions are complete in from 1 to 48 hours at −20° C. to the reflux temperature of the solution. For example, the preferred conditions for the dehydration of hemiacetal VI employ thiocarbonyl diimidazole (TCDI) with diisopropylethylamine (Hunig's base) in methylene chloride as shown in Scheme 3 to prepare Compound X. Compound X may be converted to compound XI by conventional hydrogenation procedures known to those skilled in the art, for example under conditions analogous to the reductions of m and IV above. The preferred conditions utilize 1 atmosphere of hydrogen with catalytic 10% palladium on carbon in ethyl acetate solvent.

Compounds of formula I wherein $R_1$ is a methyl, $R_2$, $R_3$ and $R_4$ are hydrogen, may be prepared in an analogous fashion to the synthesis of compound XI above. The preferred conditions utilize 1 atmosphere of hydrogen with catalytic 10% palladium on carbon in ethyl acetate solvent as shown in Scheme 4 for the synthesis of IXV, subsequent to silyl group removal using conditions described above, preferably with PPTS in ethanol.

Scheme 4

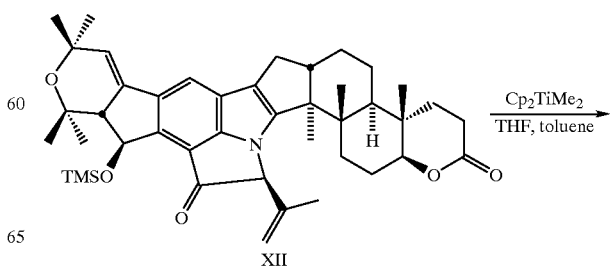

-continued

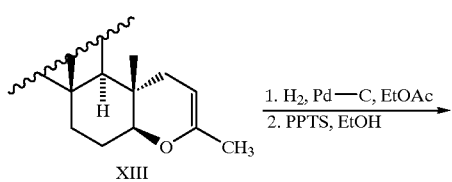
XIII

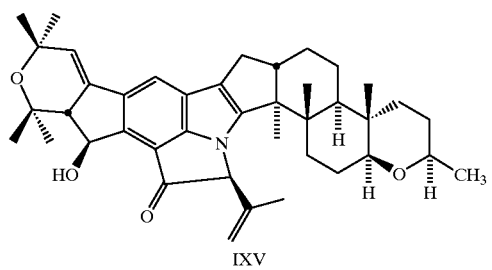
IXV

Compounds of formula I wherein $R_1$ is a phosphate $(OP(O)(OR^b)2)$ or sulfonate $(OSO_2R^b)$, $R_3$ is hydrogen, and $R_2$ and $R_4$ together form a bond across the carbon atoms to which they are attached, may be prepared according to the procedure shown in Scheme 5 using conditions known to those skilled in the art. The lactone XII is treated with a strong base including, but not restricted to, lithium diisopropylamide, lithium bis(trimethylsilyl)amide, potassium hydride, lithium tetramethylpiperidine and the like. The resulting anion is quenched with an electrophile such as $(R^bO)_2POCl$, trifluoromethane sulfonylchloride, trifluoromethane sulfonic anhydride, N-phenyltriflimide, N-(choropyridyl)triflimide and the like. Typical media used for this transformation are aprotic organic solvents such as benzene, diethyl ether, dioxane, HMPA and the like. The reactions are complete in from 1 to 24 hours at −78° C. to the room temperature. The preferred conditions are potassium bis(trimethylsilyl)amide and $(PhO)_2POCl$ in a solvent mixture of THF and toluene to prepare ketene acetal phosphate XV.

Scheme 5

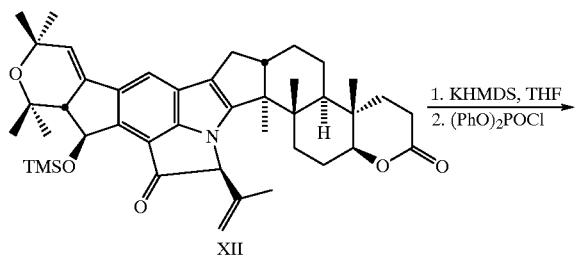
XII

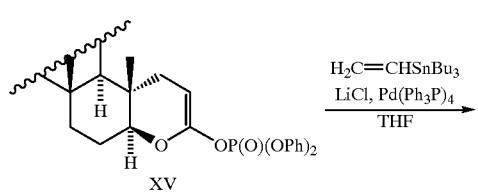
XV

-continued

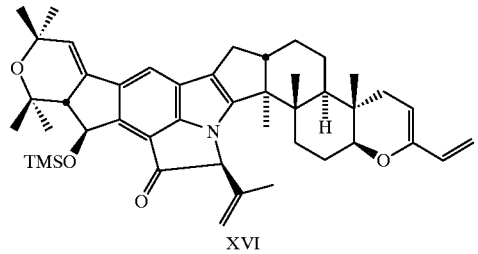
XVI

Compounds of formula I wherein $R_1$ is alkenyl, cycloalkenyl, alkynyl, alkanoyl, alkenoyl, carboxy, carboxamido, aryl or aroyl, $R_3$ is hydrogen, and $R_2$ and $R_4$ together represent a bond across the carbon atoms to which they are attached, may be prepared from the appropriate ketene acetal phosphate or sulfonate using conditions known to those skilled in the art. For example, reaction of ketene acetal phosphate XV with the appropriate stannane, boronic acid, silane, zinc reagent, carbon monoxide gas and the like, can be catalyzed by, but not restricted to, ligated palladium (O) or (I), ligated nickel (O) or (II) and the like. Other additives include, but are not restricted to, copper salts, various chloride ions, primary or secondary or tertiary amines, carbonate bases and the like. Solvents can be DMSO, dimethoxyethane, dioxane, diethyl ether, water, alcohols including, but not restricted to, methanol, also toluene, benzene, mesitylene and the like. The reactions are complete in from 1 to 72 hours at from 23° C. to the reflux temperature of the solution. The preferred conditions to prepare vinyl XVI from XV employ tributylvinylstannane, lithium chloride, palladium(O) tetrakis(triphenylphosphine) and THF solvent as shown in Scheme 5. Alternatively, XV may be converted directly to a stannane using hexamethylditin, and the like, under analogous palladium coupling conditions described above. The resultant stannane of XV can then react with acid chlorides, alkenyl halides, cycloalkenyl halides, alkynyl halides, and the like, also under analogous palladium coupling conditions described above.

Compounds of formula I wherein n is 0, $R_1$ is optionally substituted alkyl, $R_2$, $R_3$ and $R_4$ are hydrogen, may be prepared according to the procedure shown in Scheme 6. Thus, the aldehyde (Compound IXX) is homologated to an α,β-unsaturated carbonyl such as, but not restricted to, enone XXII. Compound XXII is then converted to tetrahydrofuran XXIII under conditions analogous to, but not restricted to, silyl group removal as described above. The preferred conditions utilize pyridinium para-toluenesulfonic acid (PPTS) in ethanol solvent for the synthesis of XXIII.

Scheme 6

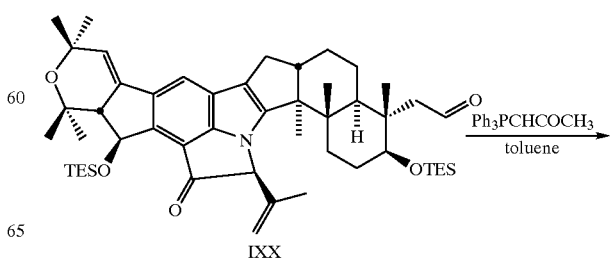
IXX

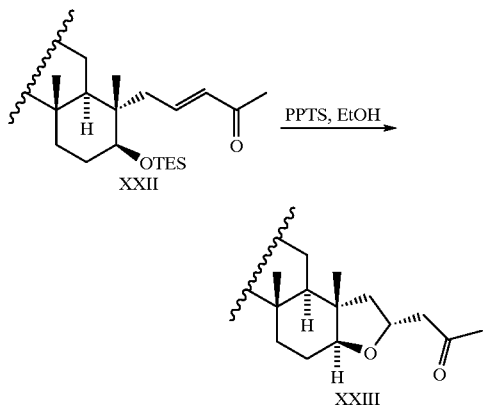

Compounds of formula I wherein $R_1$, $R_3$ and $R_4$ are hydrogen, and $R_2$ is a glycosidic linkage to a natural or unnatural mono-, di- or tri-saccharide moiety, may be prepared from hemiacetals VI and XX, or other appropriate glycosyl donors, using protocols known to those skilled in the art. For example, Compounds VI, VIII or XX may be reacted with a protected or partially protected natural or unnatural mono-, di- or tri-saccharide glycosyl acceptor under conditions that utilize reagents such as, but not restricted to, methyl triflate, trimethylsilyl triflate, DAST/SnCl$_2$, potassium bis(trimethylsilyl)amide/(PhO)$_2$P(O)Cl/trimethylsilyl triflate, Cl$_3$CCN/DBU or NaH or K$_2$C$_3$/silver triflate, tin triflate/trimethylsilyl chloride/lithium perchlorate and the like in an aprotic solvent such as methylene chloride, 1,2-dichloroethane, diethyl ether, tetrahydrofuran, benzene, toluene and the like. The glycosidation reactions are complete in from 5 minutes to 24 hours at temperatures from −78° C. to 50° C.

Compounds of formula I wherein $R_1$ and $R_4$ are each hydrogen, and $R_2$ together with $R_3$ share a bridging oxygen atom represented as an epoxide ring, may be prepared from glycal X, or other appropriate glycals, using protocols known to those skilled in the art. For example, Compound X may be epoxidized with dimethyl dioxirane, substituted oxaziridines, NBS/water/DBU, MCPBA, TBHP, peracetic acid, oxone and the like in water or an aprotic solvent such as acetone, methylene chloride, tetrahydrofuran, chloroform, benzene, toluene, acetonitrile and the like. The epoxidation reactions are complete in from 1 to 24 hours at temperatures from −78° C. to the reflux temperature of the solution.

Compounds of formula I wherein $R_1$ and $R_4$ are hydrogen, $R_2$ is hydroxy or optionally substituted oxygen or sulfur, and $R_3$ is hydroxy or optionally substituted oxygen may be prepared using various protocols known to those skilled in the art. For example, the above epoxide intermediate may be treated with neat acetic acid or acetic anhydride and pyridine with or without DMAP and with or without an added glycosyl acceptor. Alternatively, the above epoxide intermediate may be treated with any alcohol or glycosyl acceptor with the addition of, but not restricted to, ZnCl$_2$, ZrCl$_4$, Ti(Oi-Pr)$_4$, MgBr$_2$-OEt$_2$ and the like. The above reactions may be run in an aprotic solvent such as tetrahydrofuran, diethyl ether, dioxane, methylene chloride, chloroform, benzene and the like. The oxonium ion-assisted epoxide opening reactions are complete in from 5 minutes to 24 hours at temperatures from −78° C. to 23° C. Alternatively, glycal donors of formula I such as Compound X may be treated with a mixture of diphenyl sulfoxide with triflic anhydride and 2,6-di-tert-butyl-4-methylpyridine followed by triethylamine with methanol and subsequent addition of ZnCl$_2$ or Sc(OTf)$_3$ with any alcohol or glycosyl acceptor in a solvent such as methylene chloride at temperatures from −78° C. to 23° C. in from 30 minutes to 24 hours. Alternatively, glycals of formula I such as Compound X also may be dihydroxylated by treatment with, but not restricted to, osmium tetraoxide with or without the addition of co-oxidents such as, but not restricted to, N-methylmorpholine N-oxide, trimethylamine N-oxide and the like in solvents such as acetone, water, methylene chloride, tetrahydrofuran and the like. The reactions are complete in from 30 minutes to 24 hours at temperatures from −20° C. to 23° C. The vicinal diol products may be treated under anhydrous conditions with, but not restricted to, dibutyltin oxide in methanol followed by cesium fluoride in toluene and an alkyl triflate in DWF to provide glycosylation products in from 15 minutes to 24 hours at from −10° C. to 70° C.

Compounds of formula I wherein $R_1$ and $R_4$ are hydrogen, $R_2$ is hydrogen or hydroxy or optionally substituted oxygen or sulfur, and $R_3$ is amino or optionally substituted nitrogen may be prepared using various protocols known to those skilled in the art. For example, an appropriate glycal donor such as Compound X may be treated with, but not resticted to, sodium azide with ceric ammonium nitrate or PhI(OAc)$_2$ and the like, followed by acetic anhydride/sodium acetate, diphenyl diselenide, sodium nitrite, lithium bromide/silver triflate/tetramethyl urea/methanol and the like, in acetonitrile, methylene chloride and the like, in from 1 to 48 hours at from −20° C. to 60° C. The resultant azides of these reactions may be reduced to the amines under a variety of conditions known to those skilled in the art such as, but not restricted to, triphenylphosphine/THF/water, hydrogenolysis with Lindlar catalyst or other hydrogenation conditions described above, H$_2$S in an alcohol solvent and the like. The reactions are complete in from 1 to 48 hours at temperatures from 23° C. to the reflux temperature of the solution. The subsequent amines can be functionalized to include, but not restricted to, amides, ureas, carbamates, sulfonamides and the like. Alternatively, a glycal donor such as Compound X may be treated with, but not restricted to, Br$_2$NSO$_2$Ph in a solvent such as methylene chloride, followed by ammonium iodide in an alcohol solvent and treatment with potassium bis(trimethylsilyl)amide and the like, with a glycosyl acceptor in a solvent such as DMF and the like. Alternatively, a glycal donor such as Compound X also may be treated with, but not restricted to, H$_2$NSO$_2$Ph with I(sym-collidine)$_2$ClO$_4$ in a solvent such as methylene chloride, followed by treatment with lithium bis(trimethylsilyl)amide and the like, with a glycosyl acceptor in a solvent such as DMF and the like. These benzenesulfonamide forming reactions described above are complete at from −78° C. to 40° C. in from 5 minutes to 24 hours. The resultant benzenesulfonamides may be transformed into their respective amines and subsequent amides, ureas, carbamates, sulfonamides and the like, under conditions known to those skilled in the art. Alternatively, a glycal donor such as Compound X also may be treated with, but not restricted to, (saltmen)Mn(N) with trifluoroacetic anhydride in a solvent such as methylene chloride, followed by treatment with a glycosyl acceptor and borontrifluoride etherate or treatment with silica gel, H$_3$O + and the like, in from 5 minutes to 24 hours at from −78° C. to 40° C. The resultant trifluoroacetamides may be transformed into their respective amines and subsequent amides, ureas, carbamates, sulfonamides and the like, under conditions known to those skilled in the art. Lactol and phenylselenide acetal products from the above procedures may be reduced under conditions known to those skilled in the art thus converting the substituted anomeric carbons into unsubstituted methylenes.

Compounds of formula I wherein $R_3$ and $R_4$ are hydrogen, $R_1$ and $R_2$ each are oxygen and together with the carbon atom to which they are attached (anomeric carbon), form a heterocycle, more specifically referred to as a spirocyclic orthoester, may be prepared using protocols known to those skilled in the art. All possible combinations of 5- to 7-membered spirocyclic orthoesters may be ultimately prepared from hemiacetals VI and XX, or other appropriate hemiacetals, upon conversion to their respective glycals and subsequent dihydroxylation to their respective diols using protocols described above. The appropriate diol may then be mono-protected under conditions known to those skilled in the art, the lactol activated for use as a glycosyl donor under conditions described above, and converted to the anomeric phenyl selenide using, but not restricted to, PhSeH and borontrifluoride etherate. In turn the protected vicinal hydroxyl moiety may be deprotected under conditions known to those skilled in the art, and the anomeric selenide treated with, but not restricted to, DAST in methylene chloride to induce the 1,2-seleno migration providing the anomeric fluoro glycosyl donor vicinally substituted with a phenylselenide moiety. This intermediate, in turn, may be glycosylated with an appropriate mono-protected diol glycosyl acceptor under conditions described above, and the pendent hydroxyl deprotected under conditions known to those skilled in the art. The vicinal selenide may then be oxidized with, but not restricted to, sodium periodate with sodium hydrogen carbonate, MCPBA, hydrogen peroxide, ozone and the like in methylene chloride/methanol/water, TBF/water, toluene and the like. The selenoxide intermediate is then exposed to conditions including, but not restricted to, dissolution into vinyl acetate/toluene with diisopropylethylamine and heated at 140° C to affect spirocyclic orthoester formation.

Compounds of formula I wherein $R_3$ and $R_4$ are hydrogen, $R_2$ is alkoxy and RI is a carboxylic ester, may be prepared using protocols known to those skilled in the art. For example, an appropriate lactone, such as Compound IX, may be treated with, but not resticted to, bis(2,2,2-trifluoroethyl)-2-(1,3-dithiane)phosphonate with potassium bis(trimethylsilyl)amide in toluene/TBF followed by NBS and an alcohol in methylene chloride at temperatures from −78° C. to 23° C. in from 5 minutes to 12 hours.

The instant compounds are potent endo- and ecto-antiparasitic agents, particularly against helminths, ectoparasites, insects, and acarids, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, furbearing animals, zoo animals and exotic species and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have activity against these parasites, and in addition are also active against Dirofilaria in dogs and cats, Nematospiroides, Syphacia, Aspiculuris in rodents, arthropod ectoparasites of animals and birds such as ticks, mites such as scabies lice, fleas, blowflies, and other biting insects in domesticated animals and poultry, such as Tenophalides, Ixodes, Psoroptes, and Hemotobia, in sheep Lucilia sp., biting insects and such migrating dipterous larvae as Hypoderma sp. in cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly Musca domestica as well as fleas, house dust mites, termites and ants.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acreage infested with fire ant nests. The compounds are scattered above the infested area in low levels in bait formulations which are brought back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally including one or more additional active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area application, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

Accordingly, the present invention provides a method for the treatment or prevention of diseases caused by parasites which comprises administering to a host in need of such treatment or prevention an antiparasitic effective amount of a compound of Formula I. The parasites may be, for example, arthropod parasites such as ticks, lice, fleas, mites and other biting arthropods in domesticated animals and poultry. The parasites also include helminths such as those mentioned above.

Compounds of formula I are effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 500 mg per kg of animal body weight, such total dose being given at one time or in divided doses over a relatively short period of time such as 1–5 days. With the preferred compounds of the invention, excellent control of such parasites is obtained in animals by administering from about 0.025 to 100 mg per kg of body weight in a single dose. Repeat treatments are given as required to combat re-infections and are dependent upon the species of parasite and the husbandry techniques being employed. Repeat treatments may be given daily, weekly, biweekly, monthly, or longer for example up to six months, or any combination thereof, as required. The techniques for administering these materials to animals are known to those skilled in the veterinary field.

Compounds of formula I may be co-administered or used in combination with one or more other agents to the host. Co-administration or combination use includes administering all active ingredients in one formulation, for example a tablet, capsule, feed stuff, or liquid containing a compound of formula I and one or more said other agents; administering each ingredient in a separate formulation; and combinations thereof. When one or more of a compound of formula I or said other agent(s) is contained in a separate formulation, any order of administration as well as any interval between the administration of the active ingredients are within the meaning of co-administration or combination use.

Agents that may be co-administered or used in combination with compounds of formula I include any that are used in the treatment or prevention of human or animal diseases or conditions, or used in agricultural applications, or for pest control. In a preferred embodiment, the co-administered agents are used in veterinary medicine, particularly those used in domesticated animals such as dogs and cats or other companion animals. Examples of other agents that may be co-administered with compounds of formula I are provided below. It is to be understood that the specific agents enumerated are illustrative only, and are not meant to be restrictive in any manner.

Accordingly, compounds of the present invention may be co-administered or used in combination with anthelmintic agents. These anthelmintic agents are meant to include, but not be restricted to, compounds selected from the avermectin and milbemycin class of compounds such as ivermectin, avermectin, abamectin, emamectin, eprinamectin, doramectin, milbemycin derivatives described in EPO 357460, EPO 444964 and EPO 594291, moxidectin, Interceptor™ and nemadectin. Additional anthelmintic agents include the benzimidazoles such as thiabendazole, cambendazole, parbendazole, oxibendazole, mebendazole, flubendazole, fenbendazole, oxfendazole, albendazole, cyclobendazole, febantel, thiophanate and the like. Additional anthelmintic agents include imidazothiazoles and tetrahydropyrimidines such as tetramisole-levamisole, butamisole, pyrantel, pamoate, oxantel or morantel.

Compounds of this invention may be co-administered or used in combination with fipronil (FRONTLEE™); or with an insect growth regulator with molt inhibiting activity such as lufenuron (PROGRAM™) and the like; or with ecdysone agonists such as tebufenozide and the like, which induces premature molt and causes feeding to cease; or with imidacloprid (ADVANTAGE™).

Compounds of this invention may be co-administered or used in combination with avermectin or milbemycin or doramectin derivatives such as those described in U.S. Pat. No. 5,015,630, WO 94/15944, WO95/22552.

Compounds of this invention may be co-administered or used in combination with cyclic depsipeptides that exhibit anthelmintic efficacy such as those described in WO96/11945, WO93/19053, WO 93125543, EP 626375, EP 382173, WO 94/19334, EP 382173 and EP 503538.

Compounds of this invention may be used in combination or be co-administered with derivatives and analogs of the general class of dioxomorpholine antiparasitic and anthelmintic agents as illustrated by WO 9615121; or with pyrethroids or organophosphates or insecticidal carbamates, such as those described in "Chemotherapy of Parasitic Diseases", Campbell, W. C. and Rew, R. S, Eds., 1986; or with derivatives and analogs of the general class of paraherquamide and macfortine anthelmintic agents.

The co-administered compounds are given via routes, and in doses, that are customarily used for those compounds.

Compounds of formula I may be administered orally in a unit dosage form such as a capsule, bolus or tablet including chewable tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

When the compounds described herein are administered as a = component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 50% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 10% in the feed in order to achieve the desired anti-parasitic result.

In using the compounds of this invention, the individual compounds may be prepared and used in that form. Alternatively, mixtures of the individual compounds may be used, or they may be combined with other active compounds not related to the compounds of this invention.

Also included in the present invention are pharmaceutical compositions comprising a compound of formula I and a pharmaceutically acceptable carrier. The pharmaceutical compositions of the present invention may further comprise a second active ingredient such as those described above for co-administration. Preferred second ingredient is selected from an anthelmintic agent, fipronil, imidocloprid, an insect growth regulator, or a ecdysone agonist. Said second ingredient is preferably selected from the group consisting of: ivermectin, avermectin 5-oxime, abamectin, emamectin, eprinamectin, doramectin, doramectin monosaccharide 5-oximes, fulladectin, milbemycin, milbemycin 5-oxime, moxidectin, Interceptor™, nemadectin, imidacloprid, fipronil, lufenuron, thiabendazole, cambendazole, parbendazole, oxibendazole, mebendazole, flubendazole, fenbendazole, oxfendazole, albendazole, cyclobendazole, febantel, thiophanate, tetramisole-levamisole, butamisole, pyrantel, pamoate, oxantel and morantel.

The following examples are provided to more fully illustrate the present invention, and shall not be construed as limiting the scope in any manner.

REFERENCE EXAMPLE 1

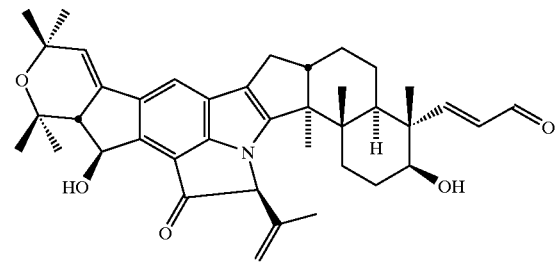

(a) Synthesis From Nodulisporic Acid

To KMnO$_4$ (3 g) at 25° C. was added water (5 mL). The KMnO$_4$ solution was cooled to 0° C. and Al$_2$O$_3$ (weakly acidic, 10.8 g) was added and stirred for 5 min until thoroughly mixed. A solution of nodulisporic acid (3 g) in CH$_2$Cl$_2$ (300 mL) was added dropwise via an addition funnel over 20 min. The solution was aged for an additional 20 min at 0° C. then at 25° C. for 90 min. The solution was filtered through a 3 inch pad of Celite using CH$_2$Cl$_2$ as eluant followed by EtOAc. The solvents were removed under reduced pressure at ambient temperature to yield pure title compound (2.234 g, 82%) without any additional purification.

(b) Synthesis From t-butyl Nodulisporamide

To N-tert-butyl nodulisporamide (50 mg) in CH$_2$Cl$_2$ (2 mL) at 25° C. was added N-methylmorpholine N-oxide (50 mg) followed by 0.024 M OsO$_4$ in water (0.31 mL). After aging the solution for 16 hr, TLC showed the presence of the desired compound and the R,R- and S,S-31,32-diols of N-tert-butyl nodulisporamide A. The title compound (10.5 mg) and the diols (36 mg) were isolated in pure form by PTLC on silica gel using 2:1 EtOAc:hexanes as eluant. The R,R- and S,S-diols were combined. To a mixture of diols (10 mg) in acetone (0.9 mL) at 25° C. was added NaIO$_4$ (25 mg) and the solution was allowed to age for 12 h. The solution was poured into saturated aqueous NaHCO$_3$, extracted with EtOAc and dried (Na$_2$SO$_4$). Pure title compound (7 mg) was obtained following PTLC on silica gel using 1/1 hexanes/EtOAc as eluant.

REFERENCE EXAMPLE 2

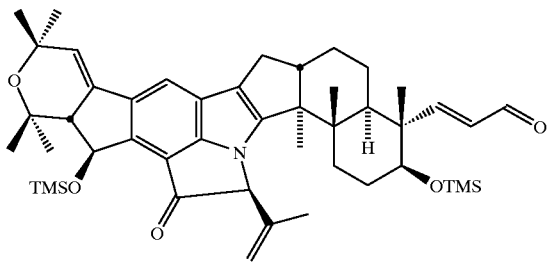

To the compound of Reference Example 1 (560 mg) in acetonitrile (10 mL) at 25° C. was added (Me₃Si)₂NH (1.8 mL) and the the solution was aged for 12 h. Additional (Me₃Si)₂NH (1.5 nL) and acetonitrile (3 mL) were then added. After 3 h, the solvent was removed under reduced pressure and the residue dried in vacuo for 1 h to yield pure title compound (870 mg, 100%) which required no purification. The product was characterized by proton NMR.

REFERENCE EXAMPLE 3

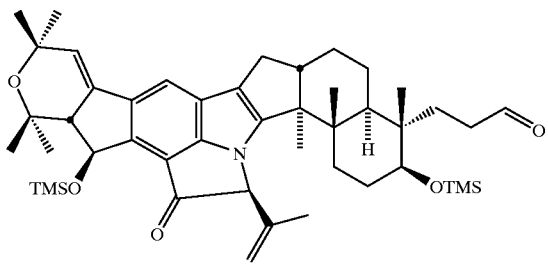

The compound of Reference Example 2 (10 mg, 0.013 mmol) was dissolved in EtOAc (1 mL), treated with a catalytic amount of 10% Pd—C and the system vacuum-purged with hydrogen. The mixture was stirred vigorously under one atmosphere of hydrogen at 23° C. for 4 h. The mixture was then filtered through a bed of celite, washed with EtOAc and the filtrate concentrated in vacuo. The product was purified (PTLC, 500 micron SiO₂, 20×20 cm, 20% acetone-hexane) to provide the title compound V (4 mg, 40%) characterized by ¹H NMR.

REFERENCE EXAMPLE 4

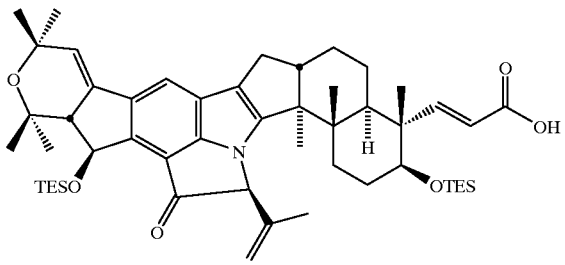

Step 1

To the compound of Reference Example 1 (750 mg) in pyridine/DMF (30 mL, 1/1) at room temperature was added Et₃SiOSO₂CF₃ (3.2 g) and aged for 20 min. The solution was diluted with ethyl acetate, washed with saturated CuSO₄ (aq) (4×), water (1×), brine (1×), and dried (Na₂SO₄). The solution was filtered, concentrated under reduced pressure and pure product was obtained following flash chromatography on silica gel using 7/93 acetone/hexanes as eluant to provide the bis-triethylsilyl protected compound of Reference Example 1.

Step 2

Method A

To the product of Step 1 (1 g) in tBuOH (25 mL) at 25° C. was added 2-methyl-2-butene (6 mL) and stirred for 5 min. A solution of NaClO₂ (954 mg) and NaH₂PO₄.2H₂O (1.28 g) in water (10 mL) was then added. After 4 h, the solution was poured into saturated NH₄Cl(aq), extracted with CH₂Cl₂ (3×) and dried (Na₂SO₄). The solution was filtered and concentrated to dryness under reduced pressure. Pure title compound (725 mg) was obtained following flash chromatography on silica gel using gradient elution (5%→25% EtOAc in hexanes).

Method B

A solution of KMnO₄ (1.3 g) in acetone (64 mL) and pH 7 phosphate buffer (21 mL) was prepared. To the product of Step 1 (3.63 g) in acetone (64 mL) was added the KMnO₄/buffer solution (~20 mL) and the solution was aged for 30 min. Additional KMnO₄ solution (~20 mL) was added every 30 min for 2 h. The solution was then cooled to 0° C. and 1M Na₂SO₃ was added until all of the KMnO₄ was reacted. The mixture was filtered and washed with 15/85 MeOH/acetone (2×). The filtrate was concentrated under reduced pressure to dryness and redissolved in water. The aqueous solution was extracted with 3/7 iPrOH/CHCl₃ (3×) and the organic layers were dried (Na₂SO₄). The solids were removed by filtration and the solution was evaporated to drynesss under reduced pressure. Pure title product (1.29 g) along with recovered starting aldehyde (~1.3 g) was obtained following flash chromatography on silica gel using 2/8 EtOAc/hexanes as eluant.

REFERENCE EXAMPLE 5

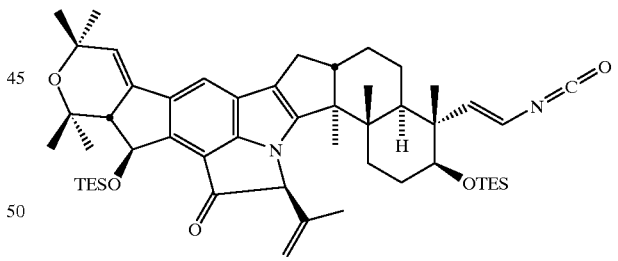

The compound of Reference Example 4 (150 mg, 0.173 mmol) was dissolved in dry CH₂Cl₂ (3.5 mL) and treated with triethylamine (0.075 mL, 0.519 mmol) followed by DPPA (0.057 mL, 0.260 mmol). The reaction mixture was maintained at 23° C. for 14 h, concentrated in vacuo and purified (PTLC, 1500 micron SiO₂, 20×20 cm, 2 plates, 10% acetone-hexane) to provide the intermediate acyl azide (150 mg, 97%). This material (150 mg, 0.168 mmol) was immediately dissolved in dry toluene (3.4 mL) under nitrogen and heated at 80° C. for 2 h. The mixture was cooled, concentrated in vacuo and vacuum pumped to dryness to provide the title compound XVIII (140 mg, 96%) characterized by ¹H NMR.

REFERENCE EXAMPLE 6

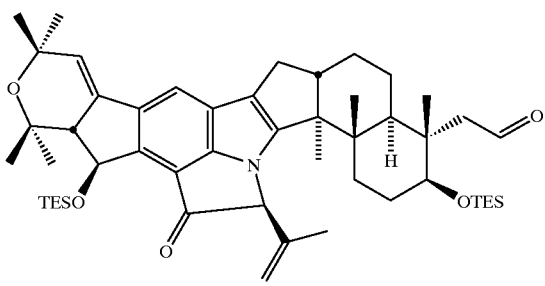

The compound of Reference Example 5 (140 mg, 0.162 mmol) was dissolved in 9:1 dioxane:H$_2$O (8 mL) and treated with 50% PPTS (20 mg, 0.081 mmol). The reaction mixture was aged at 23° C. for 4 h, partitioned between saturated NaHCO$_3$(aq) and CH$_2$Cl$_2$, the organic phase dried over sodium sulfate and concentrated in vacuo. The product was purified by centrifugal thin layer chromatography (chromatotron, 2 mm SiO$_2$, hexane to 20% EtOAc-hexane gradient elution) to provide the title compound (70 mg, 52%) characterized by $^1$H NMR.

REFERENCE EXAMPLE 7

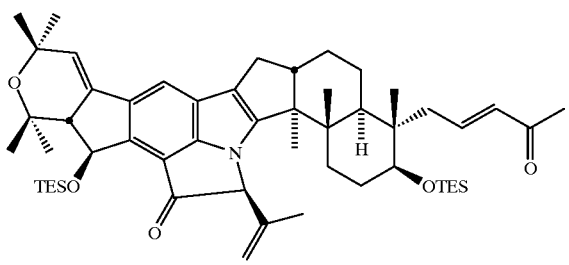

The compound of Reference Example 6 (6 mg, 0.007 mmol) was dissolved in dry toluene (0.4 mL) and treated with the stabilized ylide Ph$_3$PCHCOCH$_3$ (9 mg, 0.028 mmol). The reaction mixture was maintained at 80° C. for 20 h, concentrated in vacuo and purified (PTLC, 250 micron SiO$_2$, 20×20 cm, 10% EtOAc-hexane) to provide the title compound (3 mg, 50%) characterized by $^1$H NMR.

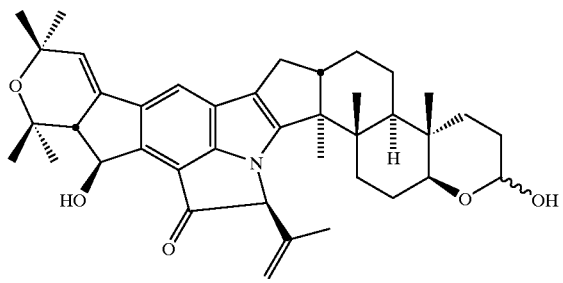

Method A

The compound of Reference Example 1 (1.2 g, 1.93 mmol) was dissolved in EtOAc (100 mL), treated with a catalytic amount of 10% Pd—C, and the system vacuum-purged with hydrogen. The mixture was stirred vigorously under one atmosphere of hydrogen at 23° C. for 5 h. The mixture was then filtered through a bed of celite, washed with EtOAc, and the filtrate concentrated in vacuo. The product was purified by flash chromatography (Biotage 40M, SiO$_2$, hexane to 30% EtOAc-hexane gradient elution) to provide the title compound (890 mg, 74%) characterized by $^1$H NMR, HPLC and mass spectrometry (m/z: 626 (M$^+$+1)).

Method B

Compound of Reference Example 3 (4 mg, 0.005 mmol) was suspended in THF (0.5 mL), treated with PPTS (2.5 mg, 0.0104 mmol) and the turbid mixture stirred vigorously at 23° C. for 14 h to provide after purification (PTLC, 500 micron SiO$_2$, 20×10 cm, 30% acetone-hexane) the title compound characterized by $^1$H NMR.

EXAMPLE 2

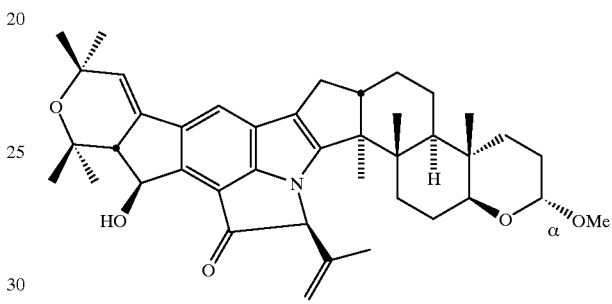

The compound of Example 1 (400 mg, 0.640 mmol) was dissolved in anhydrous MeOH (64 mL), treated with PPTS (321 mg, 1.28 mmol), and the reaction mixture was aged at 23° C. for 3 h. The mixture was then concentrated in vacuo and purified by flash chromatography (Biotage 40M, SiO$_2$, hexane to 50% EtOAc-hexane gradient elution) to provide the title compound (325 mg, 80%) characterized by $^1$H NMR, HPLC and mass spectrometry (m/z: 640 (M$^+$+1)).

EXAMPLES 3–24

The following acetals were prepared under conditions similar to those described in Example 2 using 50 molar equivalents of a given alcohol in either anhydrous THF or DMP solvent at a concentration of 0.01 M. The ethyl acetal in Example 3 was obtained from a reaction mixture conducted in neat ethanol. The following acetals were characterized by $^1$H NMR, HPLC and mass spectrometry.

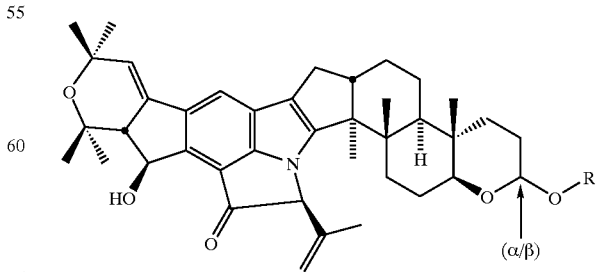

| EXAMPLE | R Group | Stereo-chemistry | Mass Spectrum (m/z) |
|---|---|---|---|
| 3 | —CH$_2$CH$_3$ | α | 654 (M$^+$ + 1) |
| 4 | —CH$_2$CH$_2$CH$_3$ | α | 668 (M$^+$ + 1) |
| 5 | —CH$_2$CH$_2$CH$_3$ | β | 668 (M$^+$ + 1) |
| 6 | —CH(CH$_3$)$_2$ | α | 668 (M$^+$ + 1) |
| 7 | —CH(CH$_3$)$_2$ | β | 668 (M$^+$ + 1) |
| 8 | —C(CH$_3$)$_3$ | α | 682 (M$^+$ + 1) |
| 9 | —CH$_2$CH=CH$_2$ | α | 666 (M$^+$ + 1) |
| 10 | —CH$_2$CH=CH$_2$ | β | 666 (M$^+$ + 1) |
| 11 | —(CH$_2$)$_6$CO$_2$CH$_3$ | α | 768 (M$^+$ + 1) |
| 12 | —CH$_2$Ph | α | 716 (M$^+$ + 1) |
| 13 | —CH$_2$-(pyrrolidinone) | α *(S) | 723 (M$^+$ + 1) |
| 14 | —CH$_2$-(pyrrolidinone) | α *(R) | 723 (M$^+$ + 1) |
| 15 | —(CH$_2$)$_2$N(H)COCH$_3$ | α | 711 (M$^+$ + 1) |
| 16 | —(CH$_2$)CH(CH$_3$)*COCH$_3$ | α *(R/S) | 710 (M$^+$ + 1) |
| 17 | —(CH$_2$)$_2$-(pyrrolidinone) | α | 737 (M$^+$ + 1) |
| 18 | —(CH$_2$)$_2$-(succinimide) | α | 751 (M$^+$ + 1) |
| 19 | —(CH$_2$)$_2$-(succinimide) | β | 768 (M$^+$ + NH$_4$) |
| 20 | —(CH$_2$)$_2$CN | α | 679 (M$^+$ + 1) |
| 21 | —CH$_2$-(furyl) | α | 706 (M$^+$ + 1) |
| 22 | —CH$_2$-(imidazolyl) | α | 706 (M$^+$ + 1) |
| 23 | —(CH$_2$)$_2$-(methylthiazolyl) | α | 751 (M$^+$ + 1) |
| 24 | —(CH$_2$)$_2$OCOC(CH$_3$)=CH$_2$ | α | 738 (M$^+$ + 1) |

EXAMPLE 25

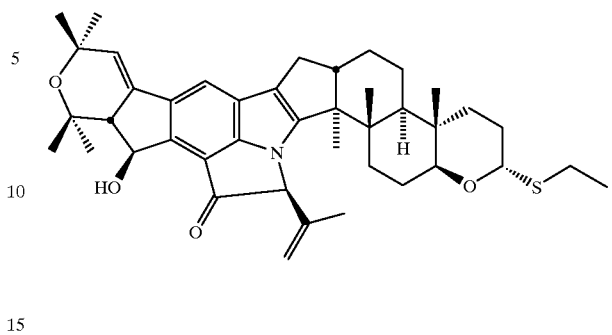

In a three-neck round bottom flask, the compound of Example 1 (20 mg, 0.032 mmol) was dissolved in anhydrous CH$_2$Cl$_2$ (0.5 mL), then treated with ethanethiol (0.5 mL), followed by PPTS (32 mg, 0.128 mmol) and the reaction mixture was aged at 23° C. for 12 h. One of the flask necks was fitted with a nitrogen inlet tube, and another neck was fitted with an outlet tube that was submerged in aqueous bleach. After the volatiles were removed via nitrogen purging, the remaining residue was purified (PTLC, 500 micron SiO$_2$, 20×20 cm, 20% acetone-hexane) to provide the title compound (15 mg, 70%) characterized by $^1$H NMR, HPLC and mass spectrometry (m/z: 670 (M$^+$+1)).

EXAMPLES 26–28

Using reaction conditions similar to those described in Example 25, the following thioacetals were prepared employing a modified work-up procedure. The crude reaction mixtures were first eluted through a short plug of SiO$_2$ and washed with hexane to remove excess thiol. Following product elution with acetone, the eluent was concentrated, and the residue was purified as described in Example 25.

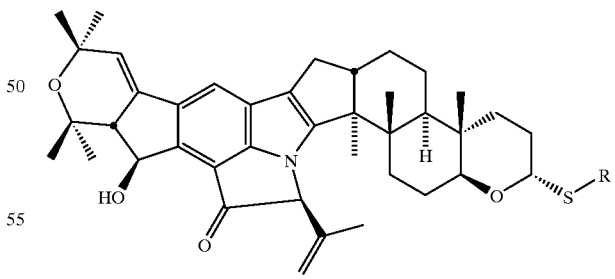

| EXAMPLE | R Group | MS (m/z) |
|---|---|---|
| 26 | —(CH$_2$)$_2$N(H)COCH$_3$ | 727 (M$^+$ + 1) |
| 27 | -Ph | 718 (M$^+$ + 1) |
| 28 | -Ph(2-OMe) | 748 (M$^+$ + 1) |

EXAMPLE 29

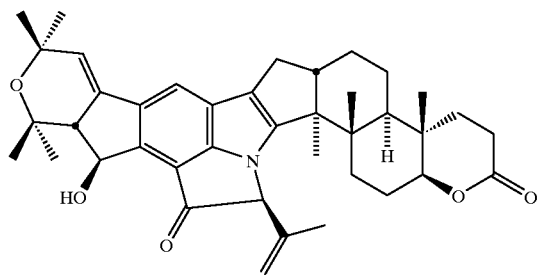

The compound of Example 1 (500 mg, 0.800 mmol) and NMO (281 mg, 2.40 mmol) were dissolved in anhydrous CH2Cl₂ (40 mL) and treated with activated powdered molecular sieves. Under an atmosphere of nitrogen, the reaction mixture was cooled to 0° C. and treated with TPAP (28 mg, 0.080 mmol). The reaction mixture was stirred at 0° C. for 2.5 h and then quenched with 20 mL of 10% NaHSO₃(aq). The mixture was then filtered through celite, partitioned between CH₂Cl₂ and brine, the organic phase dried over sodium sulfate and concentrated in vacuo to provide the title compound (500 mg, 100%) characterized by ¹H NMR, HPLC and mass spectrometry (m/z: 624 (M⁺+1)).

EXAMPLE 30

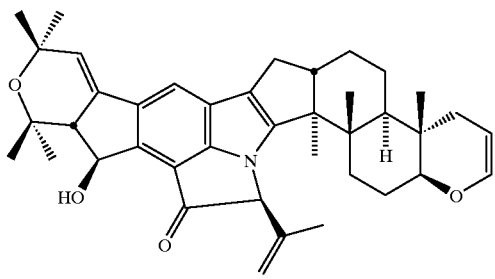

The compound of Example 1 (430 mg, 0.688 mmol) was dissolved in anhydrous CH₂Cl₂ (7 mL) and treated with diisopropylethylamine (0.38 mL, 2.06 mmol) and thiocarbonyl diimidazole (184 mg, 1.03 mmol) at 0° C. under an atmosphere of nitrogen. The reaction mixture was stirred at 0° C. for 14 h and then concentrated in vacuo to provide a residue which was purified by centrifugal thin layer chromatography (chromatotron, 4 mm SiO₂, hexane to EtOAc gradient elution). The title compound (111 mg, 27%) was characterized by ¹H NMR, BPLC and mass spectrometry (m/z: 590 (M⁺+1-H₂O)).

EXAMPLE 31

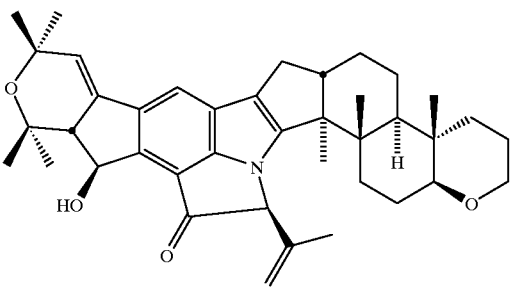

The compound of Example 30 (9 mg, 0.015 mmol) was dissolved in EtOAc (1 mL), treated with a catalytic amount of 10% Pd—C and the system vacuum-purged with hydrogen. The mixture was stirred vigorously under one atmosphere of hydrogen at 23° C. for 25 min. The mixture was then filtered through a bed of celite, washed with EtOAc and the filtrate concentrated in vacuo. The product was purified (PTLC, 250 micron SiO₂, 20×20cm, 40% EtOAc-hexane) to provide the title compound (9 mg, 100%) characterized by ¹H NMR, TPLC and mass spectrometry (m/z: 610 (M⁺+1)).

EXAMPLE 32

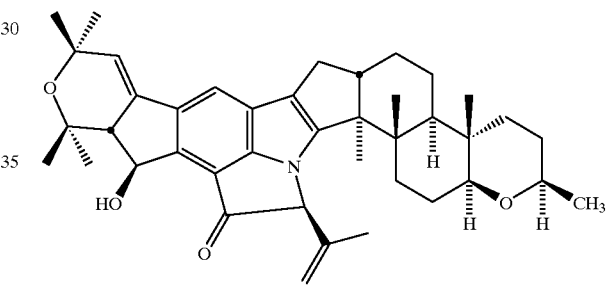

Step 1

The compound of Example 29 (500 mg, 0.800) was dissolved in anhydrous CH₃CN (15 mL) and treated with HMDS (0.85 mL, 4.00 mmol) under nitrogen at 23° C. The reaction mixture was maintained for 1 h, concentrated in vacuo and purified by centrifugal thin layer chromatography (chromatotron, 4 mm SiO₂, hexane to 60% EtOAc-hexane gradient elution) to provide the intermediate 4-O-TMS of the compound of Example 29 (420 mg, 76%) characterized by ¹H NMR.

Step 2

The product of Step 1 (30 mg, 0.0432 mmol) was dissolved in anhydrous TBF (0.87 mL) and treated with dimethyltitanocene (0.26 mL, 1M in toluene). The reaction mixture was bubbled with nitrogen to remove residual oxygen, and the mixture was then heated at 70° C. for 4 h. The mixture was cooled and concentrated in vacuo to a residue which was subsequently purified (PTLC, 500 micron SiO₂, 20×20 cm, 20% acetone-hexane) to provide intermediate (4-O-TMS 30,31-unsaturated title compound, 10 mg, 40%) characterized by ¹H NMR.

Step 3

The product of step 2 (10 mg, 0.014 mmol) was dissolved in EtOAc (1.4 mL), treated with a catalytic amount of 10% Pd—C and the system vacuum-purged with hydrogen. The mixture was stirred vigorously under one atmosphere of hydrogen at 23° C. for 5.5 h. The mixture was then filtered through a bed of celite, washed with $CH_2Cl_2$ and the filtrate concentrated in vacuo. The residue was purified (PTLC, 250 micron $SiO_2$, 20×20 cm, 20% acetone-hexane) to provide one isomeric product (5 mg, 50%) which was dissolved in EtOH (1 mL) and treated with excess PPTS at 23° C. for 10 min. The reaction mixture was concentrated in vacuo and purified (PTLC, 250 micron $SiO_2$, 20×10 cm, 15% ethyl acetate-hexane, developed 4×) to provide the title compound (2 mg, 50%) which was characterized by $^1H$ NMR, HPLC and mass spectrometry (m/z: 624 ($M^++1$)).

EXAMPLE 33

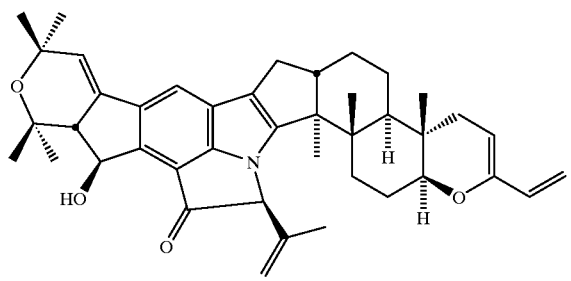

Step 1

The product of Step 1, Example 32 (90 mg, 0.130 mmol) was dissolved in dry TBF (0.4 mL), cooled to −78° C. under nitrogen and treated with a,KHMDS (0.44 mL, 0.5 M toluene). The mixture was aged for 20 min and then treated with a solution of $(PhO)_2POCl$ (0.21 mL, 1.04 mmol) in TBF (0.4 mL). The mixture was aged at −78° C. for 1 h with monitoring by TLC ($Et_3N$ vapor pre-treated $SiO_2$, 20% EtOAc-hexane eluent). The mixture was reverse quenched from −78° C. into a 0° C. solution of 1:10 $NH_4OH:H_2O$ (1.5 mL) and maintained 10 min. This solution was then partitioned at 23° C. between 1% $Et_3N-CH_2Cl_2$ and brine. The organic phase was separated, dried over sodium sulfate and concentrated to a turbid solution. This solution was treated with excess $Et_2O$, filtered through celite to remove the precipitate, and the filtrate was concentrated to an oily solid. The residue was purified by dilution into a slurry with 1% $Et_3N$-hexane followed by flash column chromatography of this slurry using hexane as eluent (3×12 cm, $SiO_2$ pre-treated with 1% $Et_3N$-hexane) to provide the intermediate shown below (80 mg, 67%) characterized by $^1H$ NMR.

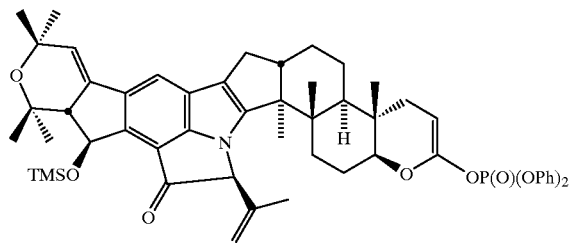

Step 2

The product of Step 1 (25 mg, 0.027 mmol) was then tared with LiCl (5 mg, 0.119 mmol), diluted under nitrogen with dry THF (0.5 mL), and then treated sequentially with vinyltributyltin (0.05 mL, 0.158 mmol) and $(Ph_3P)_4Pd$ (10 mg, 0.009 mmol). The mixture was heated at 65° C. for 12 h under TLC control ($SiO_2$, 30% EtOAc-hexane), cooled to 23° C., partitioned between saturated $NaHCO_3$(aq) and $CH_2Cl_2$, and the organic phase dried over sodium sulfate and concentrated in vacuo. The product was purified (PTLC, $SiO_2$, 1000 micron, 20×20 cm, 20% EtOAc-hexane) to give trimethylsilyl-protected title compound (4.5 mg, 25%) characterized by $^1H$ NMR.

Step 3

The product of Step 2 (2 mg, 0.003 mmol) was desilylated by treatment with PPTS (1 mg, 0.004 mmol) in EtOH (0.5 mL), and the reaction mixture was aged at 23° C. for 15 min after which the mixture was concentrated in vacuo and purified (PTLC, $SiO_2$, 250 micron, 20×10 cm, 20% acetone-hexane) to give the product alcohol shown above (1 mg, 55%) characterized by 1H NMR, BPLC and mass spectrometry (m/z: 616 ($M^++1-H_2O$)).

EXAMPLES 34

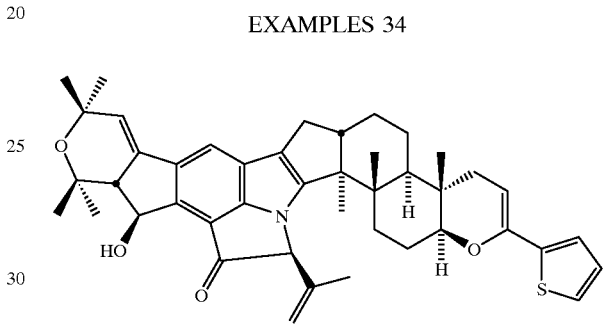

The title compound was obtained using identical reaction conditions to those described in Example 33, using 5 molar equivalents of tributyltin-2-thiophene in the palladium coupling reaction. The product was characterized by 1H NMR, HPLC and mass spectrometry (m/z: 690 ($M^++1$)).

EXAMPLE 35

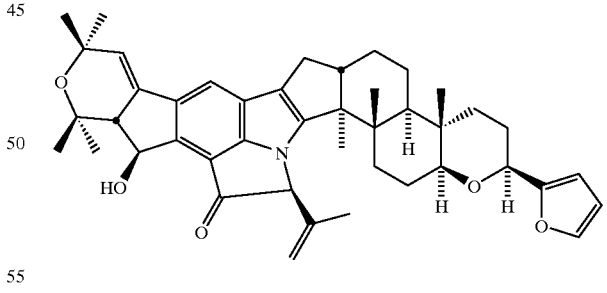

The title compound was prepared using identical reaction conditions to those described in Example 33 using 5 molar equivalents of tributyltin-2-furan in the palladium coupling reaction, with the exception that prior to the final desilylation, the product of step 2 was hydrogenated under conditions similar to those described in Example 32, step 3. The final product was purified (PTLC, 250 micron $SiO_2$, 20×10 cm, 20% acetone-hexane) to provide the title compound characterized by $^1H$ NMR.

EXAMPLE 36

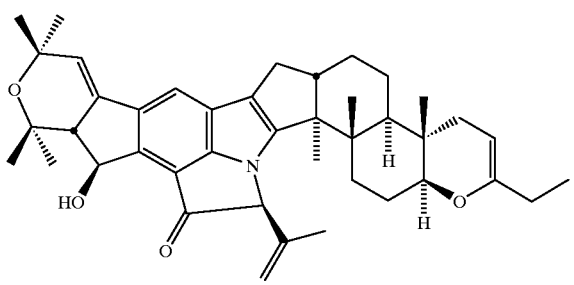

EXAMPLE 37

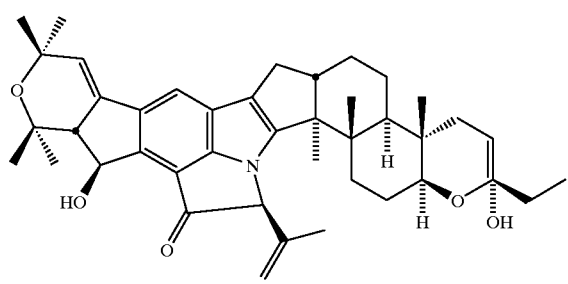

The product of Step 2, Example 33 (4 mg, 0.006 mmol) was dissolved in EtOAc (1 mL), treated with a catalytic amount of 10% Pd—C and the system vacuum-purged with hydrogen. The mixture was stirred vigorously under 1 atmosphere of hydrogen at 23° C. for 6 h. The mixture was then filtered through a bed of celite, washed with EtOAc and the filtrate concentrated in vacuo. The residue was dissolved in EtOH (0.5 mL) and treated with excess PPTS at 23° C. for 15 min. The reaction mixture was concentrated in vacuo and purified (PTLC, 250 micron $SiO_2$, 20×10 cm, 20% acetone-hexane) to provide Example 36 shown above as the less polar product (2 mg, 52%) and Example 37 shown above as the more polar product (1 mg, 25%). Both compounds were characterized by $^1H$ NMR, HPLC and mass spectrometry (Example 36 m/z: 636 ($M^++1$)) and (Example 37 m/z: 654 ($M^++1$)).

EXAMPLE 38

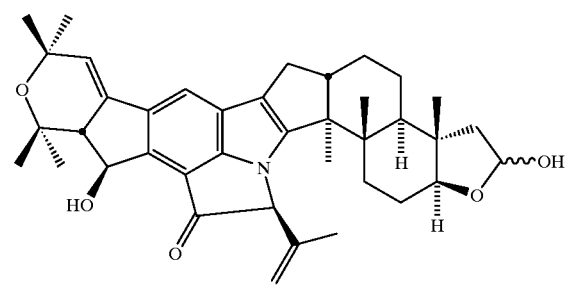

The compound of Reference Example 5 (17 mg, 0.020 mmol) was dissolved in 9:1 dioxane:$H_2O$ (1 mL) to which was added PPTS (25 mg, 0.098 mmol) followed by TsOH (4 mg, 0.020 mmol). The reaction mixture was maintained at 23° C. for 14 h, concentrated in vacuo and purified immediately (PTLC, 500 micron $SiO_2$, 20×20 cm, 30% acetone-hexane) to provide the title compound (7 mg, 60%) characterized by $^1H$ NMR, HPLC and mass spectrometry (m/z: 612 ($M^++1$)).

EXAMPLE 39

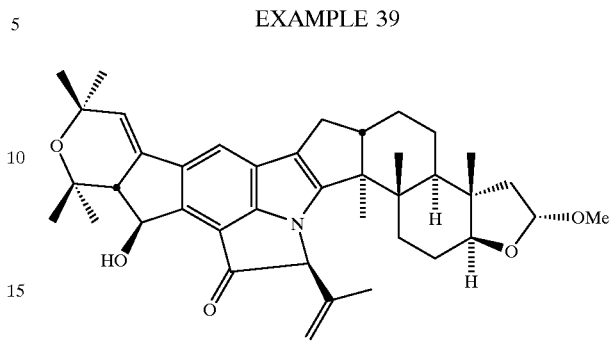

The title compound was prepared from the compound of Example 38 using similar reaction conditions to those described in Example 2. The product was purified (PTLC, 250 micron $SiO_2$, 20×10 cm, 30% acetone-hexane) to provide the title compound (5 mg, 70%) which was characterized by $^1H$ NMR, HPLC and mass spectrometry (m/z: 626 ($M^++1$)).

EXAMPLE 40

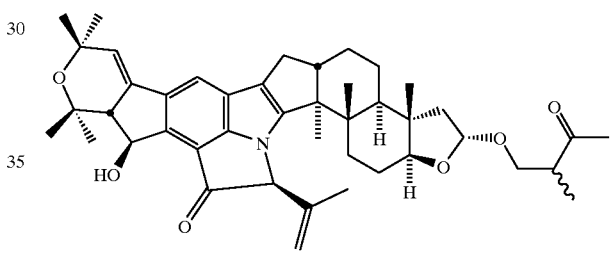

The compound of Example 38 (7 mg, 0.012 mmol) was dissolved in dry TBF (0.4 mL) and treated with racemic 3-methyl-4-hydroxy-2-butanone (0.2 mL) and PPTS (15 mg, 0.057 mmol). The reaction mixture was aged at 23° C. for 1 h and then 0° C. for 48 h. The reaction mixture was concentrated to an oil and subjected to reverse phase flash column chromatography (C-18 $SiO_2$, 1.5×4 cm, $H_2O$ to acetonitrile gradient elution) to provide semi-pure product. This material was then further purified (PTLC, 250 micron $SiO_2$, 20×20 cm, 20% acetone-hexane) to provide the title compound (5 mg, 63%) characterized by 1H NMR, HPLC and mass spectrometry (m/z: 696 ($M^++1$)).

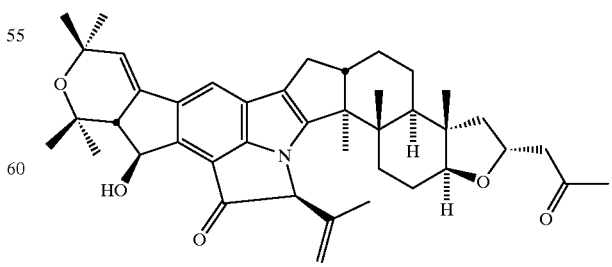

The compound of Reference Example 7 (3 mg, 0.003 mmol) was dissolved in EtOH (0.3 mL) and treated with PPTS (1 mg, 0.004 mmol). The reaction mixture was aged at 23° C. for 16 h, concentrated in vacuo and purified (PTLC, 250 micron $SiO_2$, 20×10 cm, 40% acetone-hexane) to provide the title compound (1 mg, 51%) characterized by $^1H$ NMR, HPLC and mass spectrometry (m/z: 652 ($M^+$+1)).

What is claimed is:

1. A compound having the formula I:

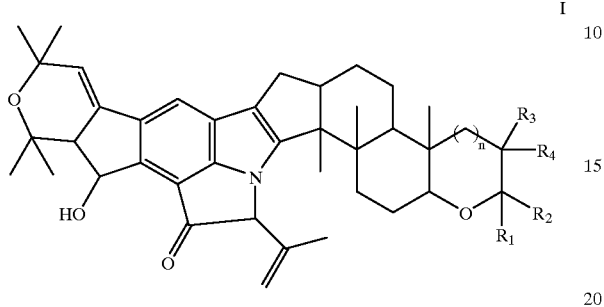

I wherein $R_1$ is
(1) hydrogen,
(2) C(O)H,
(3) substituted or unsubstituted $(C=O)_p—R^x$, wherein the substituent is one to ten groups independently selected from $R^z$, $OR^a$, $OC(O)R^b$, $CO_2R^b$, $NR^cCOR^d$, $CONR^cR^d$, and $NR^cR^d$,
(4) $C_1-C_{10}$alkoxy,
(5) $C_1-C_{10}$alkylthio,
(6) $CO_2R^b$,
(7) $CONR^cR^d$,
(8) $CONR^cSO_2R^d$,
(9) CN, $R_2$ is
(1) hydrogen,
(2) $OR^a$,
(3) $SR^a$; or $R_1+R_2$ represent =O; or $R_1$ and $R_2$ together with the carbon atom to which they are attached form a 5- to 7-membered ring containing 0 to 2 heteroatoms selected from O, $S(O)_m$ and N, substituted or unsubstituted with 1 to 4 groups independently selected from $R^1$;

$R_3$ is
(1) hydrogen,
(2) $OR^a$,
(3) $NR^cR^d$,
(4) $NR^cCOR^d$,
(5) $NR^cSO_2R^d$,
(6) $NR^eCONR^cR^d$,
(7) $NR^cCO_2R^d$; or $R_2+R_3$ represent a bridging oxygen atom;

$R_4$ is hydrogen, or $R_2$ and $R_4$ together represents a bond between the carbon atoms to which they are attached;

$R^a$ is
(1) H,
(2) optionally substituted $R^y$,
(3) optionally substituted $C(O)R^x$,
(4) $PO(OR^b)_2$,
(5) $SO_2R^b$,
(6) a natural or unnatural mono-, di- or tri-saccharide composed of any furanose or pyranose, or combination thereof; wherein said substituent for $R^x$ and $R^y$ are 1 to 10 groups independently selected from $R^z$, hydroxy, $C_1-C_6$alkoxy, $OC(O)R^b$, $CO_2R^b$, $NR^cCOR^d$, $CONR^cR^d$, and $NR^cR^d$, $R^b$ is
(1) hydrogen
(2) optionally substituted $R^y$, wherein said substituents are 1 to 10 groups independently selected from $R^z$, hydroxy, $C_1-C_6$ alkoxy, $OC(O)C_1-C_6$alkyl, carboxy, $CO_2C_1-C_6$alkyl, $NR^cCOR^d$, $CONR^cR^d$, and $NR^cR^d$,
(3) a natural or unnatural mono-, di- or tri-saccharide composed of any furanose or pyranose, or combination thereof;

$R^c$ is
(1) hydrogen,
(2) optionally substituted $R^y$, wherein said substituents are 1 to 10 groups independently selected from $R^z$, hydroxy, $C_1-C_6$alkoxy, $OC(O)C_1-C_6$alkyl, carboxy, $CO_2C_1-C_6$alkyl, $NHCOC_1-C_6$alkyl, $CONH(C_1-C_6alkyl)$, $NH_2$, $NH(C_1-C_6alkyl)$, $N(C_1-C_6alkyl)_2$, $R^d$ is independently selected from $R^C$; or $R^c$ and $R^d$ together with the N to which they are attached form a 3- to 10-membered ring containing 0 to 2 additional heteroatoms selected from O, $S(O)_m$ and N, substituted or unsubstituted with 1 to 4 groups independently selected from Re;

$R^e$ is halogen, cyano, oxo or substituted or unsubstituted with $R^x$ wherein said substituents are 1 to 10 groups independently selected from $R^z$, hydroxy, $C_1-C_6$alkoxy, $OC(O)C_1-C_6$alkyl, carboxy, $CO_2C_1-C_6$alkyl, $NHCOC_1-C_6$alkyl, $CONH(C_1-C_6alkyl)$, $NH_2$, $NH(C_1-C_6alkyl)$, $N(C_1-C_6alkyl)_2$, $R^x$ is
(1) $C_1-C_{10}$ alkyl,
(2) $C_2-C_{10}$ alkenyl,
(3) $C_2-C_{10}$ alkynyl,
(4) $C_3-C_8$ cycloalkyl,
(5) $C_5-C_8$ cycloalkenyl,
(6) aryl,
(7) a 5- or 6-membered heterocycle containing from 1 to 4 heteroatoms selected from oxygen, sulfur and nitrogen;

$R^y$ is
(1) $C_1-C_{10}$ alkyl,
(2) $C_3-C_{10}$ alkenyl,
(3) $C_3-C_{10}$ alkynyl,
(4) $C_3-C_8$ cycloalkyl,
(5) $C_5-C_8$ cycloalkenyl,
(6) aryl,
(7) a 5- or 6-membered heterocycle containing from 1 to 4 heteroatoms selected from oxygen, sulfur and nitrogen;

$R^z$ is
(1) $C_1-C_5$ alkyl,
(2) $C_2-C_5$ alkenyl,
(3) $C_3-C_8$ cycloalkyl,
(4) aryl, optionally substituted by 1 to 4 groups selected from $C_1-C_5$ alkyl, $C_2-C_5$ alkenyl, $C_1-C_5$ alkoxy, hydroxy, amino, cyano, halogen, $OC(O)C_1-C_6$alkyl, carboxy, $CO_2C_1-C_6$alkyl, $NHCOC_1-C_6$alkyl, $CONH(C_1-C_6alkyl)$, $NH(C_1-C_6alkyl)$, $N(C_1-C_6alkyl)_2$,
(5) halogen,
(6) cyano,
(7) oxo,
(8) a 5- or 6-membered heterocycle containing from 1 to 4 heteroatoms selected from oxygen, sulfur and nitrogen optionally substituted by 1 to 4 groups selected from $C_1$–$C_5$ alkyl, $C_2$–$C_5$ alkenyl, $C_1$–$C_5$ alkoxy, hydroxy, oxo, amino, cyano, halogen, OC(O)$C_1$–$C_6$alkyl, carboxy, $CO_2C_1$–$C_6$alkyl, NHCO$C_1$–$C_6$alkyl, CONH($C_1$–$C_6$alkyl), NH($C_1$–$C_6$alkyl), N($C_1$–$C_6$alkyl)$_2$, m is 0 to 2;

n is 0 or 1;

p is 0 or 1; or a pharmaceutically acceptable salt thereof.

2. A compound of claim 1 wherein n is 0.

3. A compound of claim 1 wherein n is 1.

4. A compound of claim 1 wherein $R_1$ is H, and $R_2$ is H, OR$^a$ or SR$^a$.

5. A compound of claim 1 wherein $R_2$ is OR$^a$ or SR$^a$, wherein R$^a$ is H, substituted or unsubstituted $C_1$–$C_6$alkyl, substituted or unsubstituted $C_3$–$C_6$alkenyl, or substituted or unsubstituted aryl, wherein the substituent is 1 to 4 groups independently selected from R$^z$, hydroxy, $C_1$–$C_6$alkoxy, OC(O)R$^b$, $CO_2$R$^b$, NR$^c$COR$^d$, CONR$^c$R$^d$, and NR$^c$R$^d$.

6. A compound of claim 1, wherein $R_2$ is H, and $R_1$ is R$^x$, substituted or unsubstituted with one to ten groups independently selected from R$^z$, OR$^a$, OC(O)R$^b$, $CO_2$R$^b$, NR$^c$COR$^d$, CONR$^c$R$^d$, and NR$^c$R$^d$.

7. A compound of claim 6 wherein $R_1$ is selected from $C_{1-6}$alkyl, $C_{3-6}$alkenyl, thienyl and furanyl.

8. A compound of claim 1 having the formula:

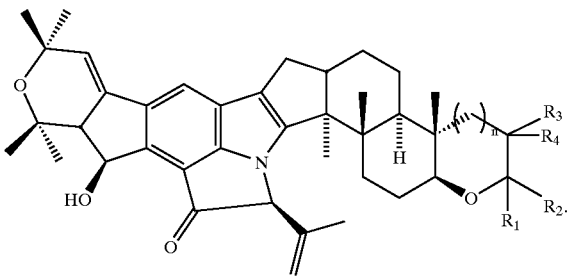

9. A compound of claim 8 wherein n is 1, $R_1$, $R_3$ and $R_4$ are each hydrogen, and $R_2$ is selected from OR$^a$ and SR$^a$, wherein R$^a$ is H, optionally substituted $C_1$–$C_6$alkyl, optionally substituted $C_3$–$C_6$alkenyl, or sub aryl, wherein the substituent is 1 to 4 groups independently selected from R$^z$, hydroxy, $C_1$–$C_6$alkoxy, OC(O)R$^b$, $CO_2$R$^b$, NR$^c$COR$^d$, CONR$^c$R$^d$, and NR$^c$R$^d$.

10. A compound of claim 8 wherein n is 1, $R_2$, $R_3$ and $R_4$ are each hydrogen, and $R_1$ is selected from R$^x$, substituted or unsubstituted with one to ten groups independently selected from R$^z$, OR$^a$, OC(O)R$^b$, $CO_2$R$^b$, NR$^c$COR$^d$, CONR$^c$R$^d$, and NR$^c$R$^d$.

11. A pharmaceutical composition comprising a compound of claim 1 and a pharmaceutically acceptable carrier.

12. A composition of claim 11 further comprising an anthelmintic agent.

13. A composition of claim 12 wherein said anthelmintic agent is selected from the group consisting of: ivermectin, avermectin 5-oxime, abamectin, emamectin, eprinamectin, doramectin, doramectin monosaccharide 5-oximes, fulladectin, milbemycin, milbamycin 5-oxime, moxidectin, Interceptor™, nemadectin, imidacloprid, fipronil, lufenuron, thiabendazole, cambendazole, parbendazole, oxibendazole, mebendazole, flubendazole, fenbendazole, oxfendazole, albendazole, cyclobendazole, febantel, thiophanate, tetramisole-levamisole, butamisole, pyrantel, pamoate, oxantel and morantel.

14. A composition of claim 11 further comprising fipronil, imidacloprid, lufenuron or an ecdysone agonist.

15. A method for the treatment or prevention of a parasitic disease in a mammal which comprises administering to said mammal an antiparasitic effective amount of a compound of claim 1.

16. A method of claim 15 further comprising administering an anthelmintic agent.

17. A method of claim 15 further comprising administering fipronil, imidacloprid or lufenuron.

* * * * *